US009441204B2

(12) United States Patent
Voorhees et al.

(10) Patent No.: US 9,441,204 B2
(45) Date of Patent: Sep. 13, 2016

(54) COMPOSITIONS AND METHODS FOR DETECTING YERSINIA PESTIS BACTERIA

(75) Inventors: Kent J. Voorhees, Golden, CO (US); Leah G. Luna, Longmont, CO (US)

(73) Assignee: COLORADO SCHOOL OF MINES, Golden, CO (US)

( * ) Notice: Subject to any disclaimer, the term of this patent is extended or adjusted under 35 U.S.C. 154(b) by 727 days.

(21) Appl. No.: 12/418,320

(22) Filed: Apr. 3, 2009

(65) Prior Publication Data

US 2009/0258341 A1 Oct. 15, 2009

Related U.S. Application Data

(60) Provisional application No. 61/042,189, filed on Apr. 3, 2008.

(51) Int. Cl.

| | |
|---|---|
| ***C12N 7/00*** | (2006.01) |
| ***C12Q 1/18*** | (2006.01) |
| ***G01N 33/543*** | (2006.01) |
| ***G01N 33/569*** | (2006.01) |

(52) U.S. Cl.

CPC . *C12N 7/00* (2013.01); *C12Q 1/18* (2013.01); *G01N 33/54306* (2013.01); *G01N 33/56911* (2013.01); *C12N 2795/10211* (2013.01); *C12N 2795/10245* (2013.01)

(58) Field of Classification Search

None

See application file for complete search history.

(56) References Cited

U.S. PATENT DOCUMENTS

| | | | |
|---|---|---|---|
| 3,839,175 | A | 10/1974 | Keyes |
| 4,104,126 | A | 8/1978 | Young |
| 4,764,473 | A | 8/1988 | Matschke |
| 4,797,363 | A | 1/1989 | Teodorescu et al. |
| 4,861,709 | A | 8/1989 | Ulitzur et al. |
| 5,085,982 | A | 2/1992 | Keith |
| 5,101,105 | A | 3/1992 | Fenselau et al. |
| 5,126,024 | A | 6/1992 | Bonelli et al. |
| 5,135,870 | A | 8/1992 | Williams et al. |
| 5,168,037 | A | 12/1992 | Entis et al. |
| 5,443,987 | A | 8/1995 | Decicco et al. |
| 5,445,942 | A | 8/1995 | Rabin et al. |
| 5,469,369 | A | 11/1995 | Rose-Pehrsson et al. |
| 5,476,768 | A | 12/1995 | Pearson et al. |
| 5,498,525 | A | 3/1996 | Rees et al. |
| 5,498,528 | A | 3/1996 | King |
| 5,550,062 | A | 8/1996 | Wohltjen et al. |
| 5,620,845 | A | 4/1997 | Gould et al. |
| 5,656,424 | A | 8/1997 | Jurgensen et al. |
| 5,658,747 | A | 8/1997 | Feldsine et al. |
| 5,679,510 | A | 10/1997 | Ray et al. |
| 5,710,005 | A | 1/1998 | Rittenburg |
| 5,723,330 | A | 3/1998 | Rees et al. |
| 5,766,840 | A | 6/1998 | Kim et al. |
| 5,789,174 | A | 8/1998 | Mouton et al. |
| 5,824,468 | A | 10/1998 | Scherer et al. |
| 5,859,375 | A | 1/1999 | Danylewych-May et al. |
| 5,874,226 | A | 2/1999 | Zeytinoglu et al. |
| 5,888,725 | A | 3/1999 | Sanders |
| 5,914,240 | A | 6/1999 | Sanders |
| 5,958,675 | A | 9/1999 | Wicks et al. |
| 5,985,596 | A | 11/1999 | Wilson |
| 6,004,770 | A | 12/1999 | Nelson |
| 6,037,118 | A | 3/2000 | Thomas et al. |
| 6,090,541 | A | 7/2000 | Wicks et al. |
| 6,093,541 | A | 7/2000 | Nelson |
| 6,177,266 | B1 | 1/2001 | Krishnamurthy et al. |
| 6,183,950 | B1 | 2/2001 | Voorhees et al. |
| 6,235,480 | B1 | 5/2001 | Shultz et al. |
| 6,265,169 | B1 | 7/2001 | Cortese et al. |
| 6,300,061 | B1 | 10/2001 | Jacobs, Jr. et al. |
| 6,316,266 | B1 | 11/2001 | Nelson |
| 6,322,783 | B1 | 11/2001 | Takahashi |
| 6,355,445 | B2 | 3/2002 | Cherwonogrodzky et al. |
| 6,428,976 | B1 | 8/2002 | Chang et al. |
| 6,436,652 | B1 | 8/2002 | Cherwonogrodzky et al. |
| 6,436,661 | B1 | 8/2002 | Adams et al. |
| 6,461,833 | B1 | 10/2002 | Wilson |
| 6,514,767 | B1 | 2/2003 | Natan |
| 6,514,778 | B2 | 2/2003 | Huang |
| 6,524,809 | B1 | 2/2003 | Wilson |
| 6,544,729 | B2 | 4/2003 | Sayler et al. |
| 6,555,312 | B1 | 4/2003 | Nakayama |
| 6,580,068 | B1 | 6/2003 | Tarver et al. |
| 6,660,437 | B2 | 12/2003 | Friedrich et al. |
| 6,660,470 | B1 | 12/2003 | Sanders |
| 6,787,360 | B2 | 9/2004 | Agrawal et al. |
| 6,799,119 | B1 | 9/2004 | Voorhees et al. |
| 6,824,975 | B2 | 11/2004 | Hubscher et al. |
| 6,913,753 | B2 | 7/2005 | Ramachandran |
| 7,034,113 | B2 | 4/2006 | Olstein |
| 7,087,376 | B2 | 8/2006 | Miller |
| 7,166,425 | B2 | 1/2007 | Madonna et al. |

(Continued)

FOREIGN PATENT DOCUMENTS

| | | |
|---|---|---|
| DE | 43 14998 | 11/1994 |
| EP | 0 168 933 | 2/1986 |

(Continued)

OTHER PUBLICATIONS

Tanji et al., Journal of Biotechnology, 2004, 114:11-20.*

Hagens et al., Appl Microbiol Biotechnol, Sep. 2007, 76(3):513-9.*

Cha et al., Biotechnol. Bioeng., 2000, 67: 565-574.*

Abbas-Hawks et al., "In Situ Methylation of Nucleic Acids Using Pyrolysis/Mass Spectrometry," Rapid Communications in Mass Spectrometry, vol. 10, pp. 1802-1806, 1996.

(Continued)

*Primary Examiner* — Nicole Kinsey White

(74) *Attorney, Agent, or Firm* — Dorsey & Whitney LLP

(57) ABSTRACT

Genetically modified bacteriophage and methods of using the same to detect bacterial types of interest are provided.

13 Claims, 10 Drawing Sheets

(56) References Cited

U.S. PATENT DOCUMENTS

| | | | |
|---|---|---|---|
| 7,195,778 | B2 | 3/2007 | Fleshner-Barak et al. |
| 2002/0192676 | A1 | 12/2002 | Madonna et al. |
| 2003/0175207 | A1 | 9/2003 | Olstein et al. |
| 2004/0002126 | A1 | 1/2004 | Houde et al. |
| 2004/0121403 | A1 | 6/2004 | Miller |
| 2004/0137430 | A1 | 7/2004 | Anderson et al. |
| 2005/0003346 | A1 | 1/2005 | Voorhees et al. |
| 2005/0208475 | A1 | 9/2005 | Best et al. |
| 2005/0250096 | A1 | 11/2005 | Wheeler et al. |
| 2005/0255043 | A1 | 11/2005 | Hnatowich et al. |
| 2007/0059725 | A1 | 3/2007 | Voorhees |
| 2007/0148638 | A1 | 6/2007 | Madonna et al. |
| 2007/0178450 | A1 | 8/2007 | Wheeler et al. |
| 2007/0249012 | A1 | 10/2007 | Lye et al. |
| 2007/0275370 | A1 | 11/2007 | Madonna et al. |
| 2009/0208996 | A1 | 8/2009 | Kadurugamuwa et al. |
| 2009/0246752 | A1 | 10/2009 | Voorhees et al. |
| 2009/0258341 | A1 | 10/2009 | Voorhees et al. |
| 2009/0286225 | A1 | 11/2009 | Wheeler et al. |
| 2009/0286232 | A1 | 11/2009 | Smith et al. |

FOREIGN PATENT DOCUMENTS

| | | | |
|---|---|---|---|
| EP | 0228975 | | 7/1987 |
| EP | 0439354 | A2 | 7/1991 |
| EP | 1300082 | A2 | 4/2003 |
| WO | WO 85/04189 | | 9/1985 |
| WO | WO 88/04326 | | 6/1988 |
| WO | WO 92/02633 | | 9/1992 |
| WO | WO 93/11161 | | 6/1993 |
| WO | WO 93/17129 | A1 | 9/1993 |
| WO | WO 94/06931 | | 3/1994 |
| WO | WO 94/13804 | | 6/1994 |
| WO | WO 95/05483 | A1 | 2/1995 |
| WO | WO 98/18962 | A1 | 5/1998 |
| WO | WO 00/10013 | | 2/2000 |
| WO | WO 01/25395 | | 4/2001 |
| WO | WO 02/06117 | A1 | 8/2002 |
| WO | WO 03/087772 | A2 | 10/2003 |
| WO | WO 03/087772 | A3 | 10/2003 |
| WO | WO 2006/012371 | | 2/2006 |
| WO | WO 2006/083292 | | 8/2006 |
| WO | WO 2006/105504 | | 10/2006 |
| WO | WO 2008/064241 | | 5/2008 |

OTHER PUBLICATIONS

Abdel-Hamid et al., "Flow-through immunofiltration assay system for rapid detection of *E. coli* O157:h7," *Biosens. Bioelectron.*, 1999, vol. 14, No. 3, pp. 309-316.

Barringer Research Limited, "Biological Agent Detection by Ion Mobility Spectrometery (Final Report)," CR96-012, pp. 1-25, Apr. 1996.

Basile et al., "Pathogenic Bacteria: Their Detection and Differentiation by Rapid Lipid Profiling with Pyrolysis Mass Spectrometry," Tends in Analytical Chemistry, vol. 00, No. 0, pp. 1-15, 1997, Elsevier Science B.V., The Netherlands.

Basile et al., "Direct Mass Spectrometric Analysis of in Situ Termally Hydrolyzed and Methylated Lipids from Whole Bacterial Cells," submitted to Analytical Chemistry, 34 pages, at least as early as Apr. 12, 2002.

Beverly et al., "A Rapid Approach for the Detection of Dipicolinic Acid in Bacterial Spores Using Pyrolysis/Mass Spectrometry," Rapid Communications in Mass Spectrometry, vol. 10, pp. 455-458, 1996.

Bird et al., "Single-Chain Antigen-Binding Proteins," *Science*, 1988, vol. 242, pp. 423-426.

Bordner et al., "Microbiological Methods for Monitoring the Environment—Water and Wastes," Dec. 1978, prepared in part under EPA Contract No. 68-03-0431, Environmental Monitoring and Support Laboratory, Office of Research and Development, USEPA, pp. i-xvi, 1-338, Cincinnati, Ohio.

Brockman et al., "Probe-Immobilized Affinity Chromatography/Mass Spectrometry", Analytical Chemistry, vol. 67, No. 24, pp. 4581-4585, Dec. 15, 1995, American Chemical Society, USA.

Bundy et al., "Lectin and Carbohydrate Affinity Caputre Surfaces for Mass Spectrometric Analysis of Microorganisms", Analytical Chemistry, vol. 73, No. 4, pp. 751-575, Feb. 15, 2001, American Chemical Society, USA.

Cairns et al., "Quantitive Models of In Vitro Bacteriophage—Host Dynamics and Their Application to Phage Therapy," *PLos Pathogens*, 2009, vol. 5, No. 1, pp. 1-10.

Cardullo, "Nonradioactive Fluorescence Resonance Energy Transfer," *Nonradioactive Labeling and Detection of Biomolecules*, C. Kessler, Editor, Springer-Verlag, New York, 1992, pp. 414-423.

Carter, "Potent antibody therapeutics by design," *Nature Reviews Immunology*, 2006, vol. 6, pp. 343-357.

Casini et al., "In vitro papillomavirus capsid assembly analyzed by light scattering," *Virology*, 2004, vol. 325, pp. 320-327.

Chatterjee et al. "A High Yielding Mutant of Mycobacteriophage L1 and Its Application as a Diagnostic Tool", FEMS Microbiology Letters, vol. 188, pp. 47-53, 2000.

Cluett et al., "The Envelope of Vaccinia Virus Reveals an Unusual Phospholipid in Golgi Complex Membranes," Journal of Cell Science, 109, pp. 2121-2131, 1996, Great Britain.

Crews et al., "Lipids Are Major Components of Human Immunodeficiency Virus: Modification of HIV Lipid Composistion, Membrane Organization, and Protein Conformation by AL-721," Drug Development Research 14:31-44, 1988.

Cudjoe et al., "Immunomagnetic Separation of Salmonella from Foods and Their Detection Using Immunomagnetic Particle (IMP)-ELISA," International Journal of Food Microbiology, Microbiology, Sep. 1995, pp. 11-25, vol. 27, No. 1, Elsevier Science, The Netherlands.

Dabrowska et al., "The effect of bacteriophages T4 and HAP1 on in vitro melanoma migration," *BMC Microbiol.*, 2009, vol. 9, pp. 9-13.

Deluca et al., Pyrolysis-Mass Spectrometry Methodology Applied to Southeasst Asian Environmental Samples for Differentiating Digested and Undigested Pollens, Analytical Chemistry, vol. 58, 2439-2442, 1986.

Deluca et al., "Direct Analysis of Bacterial Fatty Acids by Curie-Point Pyrolysis Tandem Mass Spectrometry," Analytical Chemical Society, vol. 62, No. 14, pp. 1465-1472, 1990.

Deluca et al., "Direct Analysis of Bacterial Glycerides by Curie-Point Pyrolysis-Mass Spectrometry," Journal of Analytical and Applied Pyrolysis, vol. 23, pp. 1-14, 1992, Elsevier Science Publishers B.V., The Netherlands.

Dickinson et al., "New and Improved Strategies for the Rapid Detection and Differential Identification of Microbial Spores Using MALDI-TOFMS," Proceedings of the 50th ASMS Conference on Mass Spectrometry and Allied Topics, Orlando, Florida, 2 pages; Jun. 2-6, 2002.

Dictionary.com, "Microorganism," 2009, updated, //dictionary.reference.com/browse/microorganism, pp. 1-3.

Dubow, "Bacterial Identification—Use of Phages," section in Encyclopedia Virology, 2nd Edition, R.G. Webster and A. Granoff (eds.), pp. 137-139, 1999, Academic Press, San Diego, California.

Dziadkowiec et al., "The Detection of *Salmonella* in Skimmed Milk Powder Enrichments Using Conventional Methods and Immunomagnetic Separation," Letters in Applied Microbiology, 1995, pp. 361-364, vol. 20, The Society for Applied Bacteriology, Blackwell Science, UK.

Ember, "Chemical Warfare Agent Detectors Probe the Fogs of War," C&EN, pp. 26-32, Aug. 1, 1994.

Favrin et al., "Development and Optimization of a Novel Immunomagnetic Separation-Bacteriophage Assay for Detection of *Salmonella enterica* Serovar Enteritidis in Broth," Applied and Environmental Microbiology, Jan. 2001, pp. 217-224, vol. 67, No. 1, American Society for Microbiology, Washington, D.C.

Fines et al., "Activity of linezolid against Gram-positive cocci possessing genes conferrring resistance to protein synthesis inhibitors," *J. Antimicrob. Chemoth.*, 2000, vol. 45, pp. 797-802.

Franz, et al., "Clinical Recognition and Management of Patients Exposed to Biological Warfare Agents," JAMA, vol. 278, No. 5, pp. 399-411, Aug. 6, 1997, USA.

Gantt et al., "Use of an Internal Control for Matrix-Assisted Laser Desorption/Ionization Time-of-Flight Mass Spectrometry Analysis

(56) References Cited

OTHER PUBLICATIONS of Bacteria", J Am Soc Mass Spectrom, 1999, pp. 1131-1137, vol. 10, American Society for Mass Spectrometry, Elsevier Science, The Netherlands.
Garcia, et al., "The Genome Sequence of *Yersinia pestis* Bacteriophage ϕA1122 Reveals an Intimate History with the Coliphage T3 and T7 Genomes," *Journal of Bacteriology*, Sep. 2003, vol. 185, No. 17, pp. 5248-5262.
Girault et al., "Coupling of MALDI-TOF Mass Analysis to the Separation of Biotinylated Peptides by Magnetic Streptavidin Beads," Analytical Chemistry, vol. 68, No. 13, pp. 2122-2126, Jul. 1, 1996, American Chemical Society, USA.
Goodacre et al., "Rapid Identification Using Pyrolysis Mass Spectrometry and Artificial Neural Networks of *Propionibacterium Acnes* Isolated from Dogs," Journal of Applied Bacteriology, vol. 76, pp. 124-134, 1994.
Goodridge et al., "Development and Characterization of a Fluorescent-Bacteriophage Assay for Detection of *Escherichia coli* O157:H7," *Applied and Environmental Microbiology*, Apr. 1999, vol. 65, No. 4, pp. 1397-1404.
Goodridge et al., "The use of a fluorescent bacteriophage assay for detection of *Escherichia coli* O157:H7 in inoculated ground beef and raw milk," *International Journal of Food Microbiology*, 1999, vol. 47, pp. 43-50.
Grant et al., "Isolation of *Mycobacaterium paratuberculosis* from Milk by Immunomagnetic Separation," *Applied and Environmental Microbiology*, vol. 64, No. 9, pp. 3153-3158, Sep. 1998, American Society for Microbiology, USA.
Gross et al., "Mass Spectral Studies of Probe Pyrolysis Products of Intact Oligoribonucleotides," Nucleic Acids Research, vol. 5, No. 8, pp. 2695-2704, Aug. 1978, Department of Chemistry, University of Nebraska, Lincoln, Nebraska.
Hahner et al., "Matrix-Assisted Laser Desorption/Ionization Mass Spectrometry (MALDI) of Endonuclease Digests of RHA," Nucleic Acids Research, vol. 25, No. 10, pp. 1957-1964, 1997, Oxford University Press, UK.
Haynes et al., "Surface Enhanced Raman Spectroscopy," *Anal. Chem*., 2005, pp. 339A-346A.
Heid, et al., "Real time quantitative PCR," *Genome Research*, Oct. 1996, vol. 6, No. 10, pp. 986-994.
Hendricker, "An Investigation into the Curie-point Pyrolysis-Mass Spectrometry of Glycyl Dipeptides," Journal of Analytical and Applied Pyrolysis, vol. 36, pp. 51-70, 1996.
Heylin, "The Chemicals of War," 1 page, C&EN, Mar. 9, 1998.
Higgins et al., "Competitive Oligonucleotide Single-Base Extension Combined with Mass Spectrometric Detection for Mutation Screening," BioTechniques, vol. 23, No. 4, pp. 710-714, Oct. 1997, Eaton Publishing Co., USA.
Hirsch, et al., "Rapid Detection of *Salmonella* spp. By Using Felix-O1 Bacteriophage and High-Performance Liquid Chromatography," Applied and Environmental Microbiology, vol. 45, No. 1, pp. 260-264, Jan. 1993, American Society for Microbiology, Washington, D.C.
Holland et al.,"Rapid Identification of Intact Whole Bacteria Based on Spectral Patterns Using Matrix-Assisted Laser Desorption/Ionization with Time-of-Flight Massd Spectrometry," Rapid Communications in Mass Spectrometry, vol. 10, pp. 1227-1232, 1996.
Holliger et al., "Diabodies: Small bivalent and bispecific antibody fragments," *Proc. Natl. Acad. Sci. U.S.A.*, 1993, vol. 90, pp. 6444-6448.
Holliger et al., "Engineered antibody fragments and the rise of single domains," *Nature Biotechnology*, 2005, vol. 23, No. 9, pp. 1126-1136.
Holmes et al., "Coronaviridae: The Viruses and Their Replication," Fundamental Virology, Third Edition, B.N. Fields et al. (eds.), pp. 541-559, 1996, Lippincott-Raven Publishers, Philadelphia.
Huang et al., "Interplay Between Lipids and Viral Glycoproteins During Hemolysis and Fusion by Influenza Virus," The Journal of Biological Chemistry, vol. 261, No. 28, pp. 12911-12914, 1986.
Huston et al., "Protein engineering of antibody binding sites: Recovery of specific activity in an anti-digoxin single-chain Fv analogue produced in *Escherichia coli," Proc. Natl. Acad. Sci. U.S.A*., 1988, vol. 85, pp. 5879-5883.
Jenison et al., "Silicon-Based Biosensors for Rapid Detection of Protein or Nucleic Acid Targets," Clinical Chemistry, vol. 47, No. 10, pp. 1894-1900, Oct. 2001, American Association for Clinical Chemistry, Inc.
Jenison et al., "Thin Film Biosensor for Rapid Detection of mecA from Methicillin-resistant *Staphylococcus aureus*,"Clinical Chemistry, vol. 46, No. 9, pp. 1501-1504, Sep. 2000, American Association for Clinical Chemistry, Inc.
Kermasha et al., "Comparative High-Performance Liquid Chromatographic Analyses of Cholesterol and Its Oxidation Products Using Diode-Array Ultraviolet and Laser Light-Scattering Detection," Journal of Chromatography A, vol. 685, pp. 229-235, 1994.
Kingsbury et al, "Rapid Detection and Identification of Infectious Agents," pp. i-xii, 1-296, Academic Press, Inc., Orlando, Florida 1985.
Kodikara et al., "Near On-Line Detection of Enteric Bacteria Using Lux Recombinant Bacteriophage," FEMS Microbiology Letter, vol. 83, pp. 261-265, 1991, Federation of European Microbiological Societies, Elsevier, The Netherlands.
Krishnamurthy et al., "Rapid Identification of Bacteria by Direct Matrix-assisted Laser Desorption/Ionization Mass Spectrometric Analysis of Whole Cells," *Rapid Communications in Mass Spectrometry*, 1966, vol. 10, pp. 1992-1996.
Lamoureux et al., "Detection of *Campylobacter jejuni* in Food and Poultry Viscera Using Immunomagnetic Separation and Microtitre Hybridization", Journal of Applied Microbiology, vol. 83, pp. 641-651, 1997, The Society for Applied Bacateriology, UK.
Le Cacheux et al., "Quantitative Analysis of Cholesterol and Cholesterol Ester Mixtures Using Near-Infared Fourier Transform Raman Spectroscopy," Applied Spectroscopy, vol. 50, No. 10, pp. 1253-1257, 1996.
Lech, et al., "Section III Vectors Derived from Lambda and Related Bacteriophages," *Current Protocols in Molecular Biology*, Frederick M. Ausubel, et al. (Editor), ISBN: 978-0-471-50338-5, 1987, 34 pages.
Lynn et al., "Identification of Enterobacteriaceae Bacteria by Direct Matrix-assisted Laser Desorption/Ionization Mass Spectrometric Analysis of Whole Cells," vol. 13, No. 20, pp. 2022-2027, 1999, John Wiley & Sons, Ltd., Hoboken USA.
Madonna, et al., "On-probe sample pretreatment for the detection of proteins above 15 Kda from whole cell bacteria by matrix-assisted laser desorption/ionization time-of-flight mass spectrometry," *Rapid Communications in Mass Spectrometry*, 2000, vol. 14, p. 2220-2229.
Madonna et al., "Detection of Bacteria from Biological Mixtures Using Immunomagnetic Separation Combined with Matrix-Assisted Laser Desorption/Ionization Time-of-Flight Mass Spectrometry," *Rapid Communications in Mass Spectrometry*, vol. 15, No. 13, pp. 1068-1074, Jun. 6, 2001, John Wiley & Sons, Ltd., Hoboken, USA.
Madonna et al., "Detection of *Escherichia coli* Using Immunomagnetic Separation and Bacteriophage Amplification Coupled with Matrix-assisted laser Desorption/Ionization Time-of-flight Mass Spectrometry," Rapid communications in Mass Spectrometry, published online Dec. 24, 2002 in Wiley InterScience (www.interscience.wiley.com), pp. 257-263, vol. 17, John Wiley & Sons, Ltd.
Madonna et al., "Isolation and Enrichment of *Salmonella* on Immunomagnetic Beads Prior to Detection by MALDI-TOFMS" (extended abstract), *49th ASMS Conference on Mass Spectrometry and Allied Topics*, May 27-31, 2001, Session Code: MPI, Slot: 204, 1 page, USA.
Madonna et al., "Investigation of Cell Culture Media Infected with Viruses by Pyrolysis Mass Spectrometry: Implications for Bioaerosol Detection," American Society for Mass Spectrometry, vol. 10, No. 6, pp. 502-511 Jun. 1999.
Madonna, et al., "Investigation of Viruses Using Pyrolysis Mass Spectrometry," [appears to be an internal power point presentation].

(56) References Cited

OTHER PUBLICATIONS

Mandeville et al., "Diagnostic and Therapeutic Applications of Lytic Phages," *Anal. Lett.*, 2003, vol. 36, No. 15, pp. 3241-3259.
Mansfield et al., "Immunomagnetic Separation as an Alternative to Enrichmnet Broths for *Salmonella* Detection", Letters in Applied Microbiology, vol. 16, pp. 122-125, 1993.
Marple et al., "Aerosol Sample Acquisition for Chemical and Biological Agent Detection," Abstract, Report No. ARO-25616.1-CHS, Army Research Office, Dec. 1, 1989.
Meuzelaar et al., "Characterization of Leukemic and Normal White Blood Cells by Curie-Point Pyrolysis-Mass Spectrometry. Biochemical Interpretation of Some of the Differences in the Pyrolysis Patterns," Journal of Analytical and Applied Pyrolysis, vol. 3, pp. 111-129, 1981.
Munoz-Barroso et al., "Dynamic Properties of Newcastle Disease Virus Envelope and Their Relations with Viral Hemagglutinin-Neuraminidase Membrane Glycoprotein," Biochimica et Biophysica Acta, vol. 1327, pp. 17-31, 1997.
Nakamura et al., "A Visualizatoin Method of Filamentous Phage Infection and Phage-Derived Proteins in *Escherichia coli* Using Biotinylated Phages," Biophysical and Biophysical Research Communications, vol. 289, No. 1, pp. 252-56 Nov. 2001.
Nelson et al., "Mass Spectrometric Immunoassay", Analytical Chemistry, vol. 67, No. 7, pp. 1153-1158, Apr. 1, 1995, American Chemical Society, USA.
Nyiendo, et al., "Preparation and Storage of High-Titer Lactic *Streptococcus* Bacteriophages," Applied Microbioilogy, vol. 27, No. 1, pp. 72-77, Jan. 1974, American Society for Microbiology.
Okrend et al., "Isolation of *Escherichia coli* O157:H7 Using O157 Specific Antibody Coated Magnetic Beads", *Journal of Food Protection*, Mar. 1992, pp. 214-217, 55, International Association of Milk, Food and Environmental Sanitarians.
Olsvik et al., "Magnetic Separation Techniques in Diagnostic Microbiology," Clinical Microbiology Reviews, vol. 7 No. 1, pp. 43-54, Jan. 1994.
Ostlund et al., "Quantification of Cholesterol Tracers by Gas Chromotography-Negative Ion Chemical Ionization Mass Spectrometry," Journal of Mass Spectrometry, 31:1291-1296, 1996.
Patzer et al., "Lipid Organization of the Membrane of Vesicular Stomatitis Virus," The Journal of Biological Chemistry, vol. 253, No. 13, pp. 4544-4550, Jul. 1978.
Pugh et al., "A Complete Protocol Using Conductance for Rapid Detection of *Salmonellas* in Confectionary Materials," Letters in Applied Microbiology, 1988, p. 23-27, vol. 7, The Society for Applied Microbiology, Blackwell Science, UK.
Pyle et al., "Sensitive Detection of *Escherichia coli* O157:H7 in Food and Water by Immunomagnetic Separation and Solid-Phase Laser Cytometry", Applied and Environmental Microbiology, May 1999, pp. 1966-1972, vol. 65, No. 5, American Society for Microbiology, Washington, D.C.
Rowe et al., "An Array Immunosensor for Simultaneous Detection of Clinical Analytes", *Analytical Chemistry*, Jan. 15, 1999, 71-#2, American Chemical Society, USA.
Ryzhov et al., "Characterization of the Protein Subset Desorbed by MALDI from Whole Bacterial Cells," Analytical Chemistry, Feb. 15, 2001, pp. 746-750, vol. 73, No. 4, American Chemical Society, Washington, D.C.
Sambrook et al., *Molecular Cloning: A Laboratory Manual*, Second Edition, 1889, Cold Spring Harbor Laboratory Press, 27 pages (Title page and Table of Contents).
Sanderson, et al., "Surface Sampling Methods for Bacillus anthracis Spore Contamination," Emerging Infectious Diseases, vol. 8, No. 10, pp. 1145-1151, Oct. 2002.
Schlesinger, "Detecting Battlefield Toxins," Popular Science, 2 pages Oct. 1998.
Siuzdak, "Probing Viruses with Mass Spectrometry," *Journal of Mass Spectrometry*, vol. 33, pp. 203-211, 1998, John Wiley & Sons Ltd.
Skjerve et al., "Detection of *Listeria monocytogenes* in Foods by Immunomagnetic Separation," Applied and Environmental Microbiology, Nov. 1990, pp. 3478-3481, vol. 56, No. 11, American Society for Microbiology, Washington, DC.
Stankiewicz et al., "Assessment of Bog-body Tissue Preservation by Pyrolysis-Gas Chromatography/Mass Spectrometry," Rapid Communications in Mass Spectrometry, vol. 11, pp. 1884-1890, 1997.
Stewart et al., "The specific and sensitive detection of bacterial pathogens within 4 h using bacteriophage amplification," Journal of Applied Microbiology, vol. 84, pp. 777-783, 1998, The Society for Applied Microbiology, Blackwell Science, U.K.
Stewart, "In vivo bioluminescence: new potentials for microbiology," Letters in Applied Microbiology, vol. 10, pp. 1-8, 1990, The Society for Applied Microbiology, Blackwell Science, UK.
Strauss, et al., "Purification and Properties of Bacteriophage MS2 and of its Ribonucleic Acid, " J. Mol. Biol., vol. 7, pp. 43-54, 1963, Elsevier Science, The Netherlands.
Sun et al., Use of Bioluminescent *Salmonella* for Assessing the Efficiency of Constructed Phage-Based Biosorbent, *Journal of Industrial Microbiology & Biotechnology*, 2000, vol. 25, pp. 273-275, Nature Publishing Group.
Sun et al., "Use of Bioluminescent *Salmonella* for Assessing the Efficiency of Constructed Phage-Based Biosorbent," Journal of Industrial Microbiology & Biotechnology, vol. 27, No. 2, pp. 126-28, Aug. 2001.
Tan et al., "Rapid Simultaneous Detection of Two Orchid Viruses Using LC- and/or MALDI-mass Spectrometry," *Journal of Virological Methods*, vol. 85, pp. 93-99, 2000, Elsevier Science B.V., The Netherlands.
Tas et al., "Characterization of Virus Infected Cell Cultures by Pyrolysis/Direct Chemical Ionization Mass Spectrometry," Biomedical and Environmental Mass Spectrometry, vol. 18, pp. 757-760, 1989.
Thomas et al., "Viral Characterization by Direct Analysis of Capsid Proteins," Analytical Chemistry, vol. 70, No. 18, pp. 3863-3867, Sep. 15, 1998.
Tomlinson et al., "Methods for Generating Multivalent and Bispecific Antibody Fragments," *Methods Enzymol.*, 2000, vol. 326, pp. 461-479.
Tremblay, "DARPA Expands R&D on Biowarfare Defense Tools," 1 page, C&EN, Feb. 16, 1998.
Van De Plas et al., "Colloidal Gold as a Marker in Molecular Biology: The Use of Ultra-Small Gold Particles," *Nonradioactive Labeling and Detection of Biomolecules*, C. Kessler, Editor, Spring-Verlag, New York, 1992, pp. 116-126.
Van Der Wolf et al., "Immunomagnetic separation of *Erwinia caratovora* subsp. Astroseptica from potato peel extracts to improve detection sensitivity on a crystal violet pectate medium or by PCR," Journal of Applied Bacteriology, vol. 80, pp. 487-495, May 1996, Blackwell Science, UK.
Van Hoeven et al., "Studies on Plasma Membranes," Biochimica et Biophysica Acta, vol. 380, pp. 1-11, 1975, Elesevier Scientific Publication Company, The Netherlands.
Voorhees et al., "An Investigation of the Pyrolysis of Oligopeptides by Curie-point Pyrolysis-tandem Mass Spectrometry," Journal of Analytical and Applied Pyrolysis, vol. 30, pp. 1-16, 1994, Elsevier Science B.V., The Netherlands.
Wang et al., "Investigation of Spectral Reproducibility in Direct Analysis of Bacteria Proteins by Matrix-Assisted Laser Desorption/Ionization Time-of-Fight Mass Spectrometry," Rapid Communications in Mass Spectrometry, vol. 12, pp. 456-464, 1998, John Wiley & Sons, Ltd., Hoboken, USA.
Ward et al., "Binding activities of a repertoire of single immunoglobulin variable domains secreted from *Escherichia coli,*" *Nature*, 1989, vol. 341, pp. 544-546.
Windig et al., "Control of the Absence of Deae-Polysaccharides in Deae-Sephadex Purified Poliovirus Suspensions by Pryolysis Mass Spectrometry," Develop. Biol Standard, vol. 47, pp. 169-177, 1981.
Wu et al., "A hairpin aptamer-based electrochemical biosensing platform for the sensitive detection of proteins," *Biomaterials*, 2009, vol. 30, pp. 2950-2955.
Wyatt et al., "Immunoassays for Food-poisoning Bacteria and Bacterial Toxins," Nov. 1992, pp. i-xiii, 1-129, James & James (Science Publishers) Ltd. and Chapman & Hall, London, Great Britain.

(56) References Cited

OTHER PUBLICATIONS

Yates et al., "Method to Compare Collison-Induced Dissociation Spectra of Peptides: Potential for Library Searching and Subtractive Analysis," Analytical Chemisry, vol. 70, pp. 3557-3565, 1998.

Yu et al, "Immunomagnetic-Electrochemiluminescent Detection of *Escherichia coli* O157 and *Salmonella typhimurium* in Foods and Environmental Water Samples," Applied and Environmental Microbiology, vol. 62, No. 2, pp. 587-592, Feb. 1996, American Society for Microbiology, Washington, D.C.

U.S. Appl. No. 10/249,452, Non-Final Office Action dated Feb. 23, 2005, 12 pages; and corresponding response dated Aug. 26, 2005, 17 pages.

U.S. Appl. No. 10/249,452, Non-Final Office Action dated Feb. 7, 2006, 9 pages; and corresponding response dated Aug. 7, 2006, 7 pages, and supplemental response dated Aug. 30, 2006, 6 pages.

U.S. Appl. No. 10/823,294, Final Office Action dated Dec. 3, 2007, 14 pages; and corresponding response and RCE dated Mar. 3, 2008, 14 pages.

U.S. Appl. No. 10/893,294, Non-Final Office Action dated Apr. 25, 2008, 11 pages; and corresponding response dated Aug. 25, 2008, 5 pages.

U.S. Appl. No. 10/823,294, Non-Final office Action dated Jul. 23, 2007, 20 pages; and corresponding response dated Nov. 21, 2007, 24 pages.

U.S. Appl. No. 10/823,294, Non-Final Office Action dated Sep. 30, 2008, 8 pages; no response made.

* cited by examiner

GENE $\phi$13 UP REGULATED EXPRESSION -- CREATION OF RECOMBINANT $\phi$A1122 PHAGE FOR USE IN BIODETECTION ASSAY STEP 1: PCR AMPLIFICATION OF UPSTREAM GENE $\phi$13, Laq$I^q$, pTrc-rbs, AND GENE $\phi$13

| REGION TO BE AMPLIFIED | TEMPLATE | PRIMERS (BASE PAIR LENGTH) | PRIMER SEQUENCES | PRIMER SET ANNEALING Tm -5°C |
|---|---|---|---|---|
| UPSTREAM GENE$\phi$13 | PHAGE $\phi$A1122 DNA | Pa (39)<br>Pb (42) | SEQ ID NO. 1<br>TCACACGTTCCTAACTACATCGAATTCCC<br>TAATGGTGTG<br>SEQ ID NO. 2<br>GAAACCATCCCGTAATCGATGTCGTATT<br>GTTCTCCCTATAG | 58.2 |
| Laq$I^q$ | pTrcHis/CAT | Pc (42)<br>Pd (44) | SEQ ID NO. 3<br>GACACCATCATCGATGAATGGTGCAAAA<br>CCTTTCGCGTATG<br>SEQ ID NO. 4<br>CAGATCAATTCAAGCTTGCGCTAACTCA<br>CATTAATTGCGTTGCG | 60.8 |
| Ptrc-rbs | pTrcHis/CAT | Pe (41)<br>Pf (39) | SEQ ID NO. 5<br>GCAAATATTCTGAAATGAGCAAGCTTTGT<br>TGACAATTAATC<br>SEQ ID NO. 6<br>AATATGGATCCATACCTCTTTAATTTTTA<br>ATAATAAAGTTAATCG | 51.9 |
| GENE$\phi$13 | PHAGE $\phi$A1122 DNA | Pg (44)<br>Ph (45) | SEQ ID NO. 7<br>CGACTACGGGATGGTTTTCTTGGATCCA<br>TGATGACTATAAGACC<br>SEQ ID NO. 8<br>CTACCCAACACATATGGGTCGACTTATC<br>CTCCTTTCGTTATTGTG | 59.5 |

FIG.1

PHAGE ϕA1122 HOST ASSEMBLY PROTEIN SEQUENCING INFORMATION AND AMINO ACID COMPOSITION

NUCLEOTIDE POSITION:
24924-25340

REGULATORY ELEMENT:
ϕ13
GENE:
13
GENE TRANSLATION INITIATION REGION:
SEQ ID NO. 9 TACGGGATGGTTTTCTTATGATG
SHINE-DALGARNO SEQUENCE IS DOUBLE UNDERLINED AND INITIATION CODON IS UNDERLINED

NUMBER OF AMINO ACIDS:
138
PRIMARY ACCESSION NUMBER:
Q858K2
MOLECULAR MASS OF PROTEIN:
15,795 Da

AMINO ACID PROTEIN SEQUENCE:

SEQ ID NO. 10 MMTIRPTKST DFEVFTPAHH DILEAKAAGI EPSFPDASEC VTLSLYGFPL
AIGGNCGGQC WFVTSDQVWR LSGKAKREFR KLIMEYRDKM LEKYDTLWNY
VWVGNTSHIR FLKTIGAVFH EEYTRDGQFQ LFTITKGG

FIG.5

SEQUENCE LISTING

<160> NUMBER OF SEQ ID NOS: 10

<210> SEQ ID NO 1
<211> LENGTH: 39
<212> TYPE: DNA
<213> ORGANISM: Phage

<400> SEQUENCE: 1
tcacacgttc ctaactacat cgaattccct aatggtgtg 39

<210> SEQ ID NO 2
<211> LENGTH: 41
<212> TYPE: DNA
<213> ORGANISM: Phage

<400> SEQUENCE: 2
gaaaccatcc cgtaatcgat gtcgtattgt tctccctata g 41

<210> SEQ ID NO 3
<211> LENGTH: 42
<212> TYPE: DNA
<213> ORGANISM: Phage

<400> SEQUENCE: 3
gacaccatca tcgatgaatg gtgcaaaacc tttcgcggta tg 42

<210> SEQ ID NO 4
<211> LENGTH: 44
<212> TYPE: DNA
<213> ORGANISM: Phage

<400> SEQUENCE: 4
cagatcaatt caagcttgcg ctaactcaca ttaattgcgt tgcg 44

<210> SEQ ID NO 5
<211> LENGTH: 41
<212> TYPE: DNA
<213> ORGANISM: Phage

<400> SEQUENCE: 5
gcaaatattc tgaaatgagc aagctttgtt gacaattaat c 41

<210> SEQ ID NO 6
<211> LENGTH: 45
<212> TYPE: DNA
<213> ORGANISM: Phage

<400> SEQUENCE: 6
aatatggatc catacctctt taatttttaa taataaagtt aatcg 45

<210> SEQ ID NO 7
<211> LENGTH: 44
<212> TYPE: DNA
<213> ORGANISM: Phage

<400> SEQUENCE: 7
cgactacggg atggttttct tggatccatg atgactataa gacc 44

<210> SEQ ID NO 8
<211> LENGTH: 45
<212> TYPE: DNA
<213> ORGANISM: Phage

<400> SEQUENCE: 8
ctacccaaca catatgggtc gacttatcct cctttcgtta ttgtg 45

<210> SEQ ID NO 9
<211> LENGTH: 23
<212> TYPE: DNA

-continued

```
<213> ORGANISM: Phage

<400> SEQUENCE: 9

tacgggatgg ttttcttatg atg                                              23


<210> SEQ ID NO 10
<211> LENGTH: 138
<212> TYPE: PRT
<213> ORGANISM: Phage

<400> SEQUENCE: 10

Met Met Thr Ile Arg Pro Thr Lys Ser Thr Asp Phe Glu Val Phe Thr
1               5                   10                  15

Pro Ala His His Asp Ile Leu Glu Ala Lys Ala Ala Gly Ile Glu Pro
            20                  25                  30

Ser Phe Pro Asp Ala Ser Glu Cys Val Thr Leu Ser Leu Tyr Gly Phe
        35                  40                  45

Pro Leu Ala Ile Gly Gly Asn Cys Gly Gly Gln Cys Trp Phe Val Thr
    50                  55                  60

Ser Asp Gln Val Trp Arg Leu Ser Gly Lys Ala Lys Arg Glu Phe Arg
65                  70                  75                  80

Lys Leu Ile Met Glu Tyr Arg Asp Lys Met Leu Glu Lys Tyr Asp Thr
                85                  90                  95

Leu Trp Asn Tyr Val Trp Val Gly Asn Thr Ser His Ile Arg Phe Leu
            100                 105                 110

Lys Thr Ile Gly Ala Val Phe His Glu Glu Tyr Thr Arg Asp Gly Gln
        115                 120                 125

Phe Gln Leu Phe Thr Ile Thr Lys Gly Gly
    130                 135
```

COMPOSITIONS AND METHODS FOR DETECTING YERSINIA PESTIS BACTERIA

CROSS REFERENCE TO RELATED APPLICATIONS

This application claims the benefit of priority under 35 U.S.C. 119(e) of U.S. Provisional Application No. 61/042,189 entitled Compositions And Methods For Detecting Bacteria, filed Apr. 3, 2008, which is hereby incorporated by reference.

SEQUENCE LISTING

A Sequence Listing submitted in computer readable form (CRF) is hereby incorporated by reference. The CRF file is named 187575US2.ST25.txt, was created on Jun. 15, 2009, and contains 3.14 kilobytes.

FIELD

The disclosure relates generally to genetically modified bacteriophage and methods of using the same to detect target bacterial types.

BACKGROUND

It is beneficial for a method or apparatus used for the detection of pathogenic microorganisms to have the ability to quickly provide an accurate result as to the presence or absence of the microorganism in a sample. This is true for those methods and apparati used to detect bacterial agents. Portability of a detection apparatus, enabling its use in the field, is also beneficial. Many prior art methods for detecting microorganisms have involved a significant lag time between sampling and detection and have employed techniques that are not readily adapted to portable devices.

Standard microbiological methods for detecting microorganisms have relied on substrate-based assays to test for the presence of specific bacterial pathogens. Such methods typically require growing cultures of the targeted organism, which can take twenty-four hours or longer.

Alternatives to standard microbiological methods include the use of antibodies and molecular detection methods. In many such methods, antibodies are used to first trap and then separate targeted organisms from other constituents in biological mixtures. Once isolated, the captured organism can be concentrated and detected by a variety of different techniques that do not require cultivating the biological analyte.

Previously disclosed methods for detecting analyte include ELISA, dot blot assay, electrochemiluminescence, flow cytometry, and matrix-assisted laser desorption/ionization (MALDI) time-of-flight (TOF) mass spectrometry (MS).

'Polymerase Chain Reaction' (PCR)-based methods have also been used to detect specific microorganisms in a sample. Such methods typically involve extraction of the genetic material (RNA and/or DNA) from a sample, amplification of a target genetic sequence specific to the microorganism of interest, and detection of amplification products.

Methods involving the use of bacteriophage to detect bacteria of interest in a sample have also been described. Some methods employing bacteriophage have relied on detection of bacterial components released from lysed bacteria following infection, while others have relied on detection of progeny bacteriophage or biological substances associated therewith. Genetically modified bacteriophage have also been described for use in methods of bacterial detection.

Most previously disclosed bacteriophage-based schemes for the detection of bacteria require bacteriophage replication and are, accordingly, associated with a significant lag time to detection. Additionally, many previously disclosed methods for detecting microorganisms are not readily adapted for use in portable detection devices. Methods for more quickly and accurately detecting pathogenic bacteria in samples, and portable devices compatible with such methods that enable detection in the field, are highly desirable.

SUMMARY

The present disclosure derives in part from the finding that a bacteriophage gene encoding a head assembly protein is expressed, and its product may be detected, very soon following bacterial infection, particularly, during the late eclipse or early latent periods. Further, this early expressed gene product may serve as a surrogate marker for the presence of bacteria of a target bacterial type. As further established herein, genetically modified bacteriophage engineered to overexpress the head assembly protein gene, or a surrogate marker gene in its place, may be used to very quickly detect the presence of target bacteria without the need for bacteriophage replication or more than a single round of bacterial infection.

In accordance with the objectives stated above, in one aspect, the disclosure provides methods for determining the presence or absence of bacteria of a target bacterial type in a sample. The methods may comprise the steps of (i) providing a sample; (ii) contacting the sample with genetically modified bacteriophage that are selective for the target bacterial type under conditions that allow the genetically modified bacteriophage to infect the target bacteria that may be present in the sample, thereby producing a bacteriophage exposed sample, wherein the genetically modified bacteriophage comprise a recombinant bacteriophage marker gene comprising a nucleic acid sequence encoding a bacteriophage marker operably linked to an expression control region that affects expression of the bacteriophage marker gene during the late eclipse or early latent period following infection of target bacteria by the genetically modified bacteriophage; (iii) incubating the bacteriophage exposed sample for a period of time sufficient to allow the genetically modified bacteriophage to infect the target bacteria that may be present in the sample; and (iv) assaying the bacteriophage exposed sample for the bacteriophage marker encoded by the bacteriophage marker gene, wherein the assaying step does not detect the presence of the bacteriophage marker in the bacteriophage exposed sample in the absence of bacterial infection, and wherein the presence of the bacteriophage marker indicates the presence of bacteria of the target bacterial type in the sample.

In one embodiment, the method further comprises the use of a negative control, wherein steps (i)-(iv) are repeated with a control sample known to lack bacteria of the target bacterial type to confirm that the assaying step does not detect the presence of the bacteriophage marker in the bacteriophage exposed sample in the absence of bacterial infection.

In one embodiment, the nucleic acid sequence encoding a bacteriophage marker encodes an endogenous head assembly protein, and the expression control region affects overexpression of the bacteriophage marker gene encoding the endogenous head assembly protein.

In one embodiment, the nucleic acid sequence encoding a bacteriophage marker encodes a heterologous product, such as without limitation, a heterologous protein, and the expression control region affects expression of the bacteriophage marker gene encoding the heterologous product during the late eclipse or early latent period.

In one embodiment, the target bacterial type is *Yersinia pestis*. In another embodiment, the target bacterial type is *Bacillus anthracis*. In another embodiment, the target bacterial type is *Francisella tularensis*. In another embodiment, the target bacterial type is *Burkholderia mallei*. In another embodiment, the target bacterial type is *E. coli*. In another embodiment, the target bacterial type is *Staphylococcus.*

In one embodiment, the genetically modified bacteriophage is a genetically modified ϕA1122 capable of infecting *Yersinia pestis*. Numerous other bacteriophage in the art are of interest.

In one embodiment, the genetically modified bacteriophage is a genetically modified ϕA1122 capable of infecting *Yersinia pestis*, wherein the nucleic acid encoding a bacteriophage marker encodes a ϕA1122 endogenous head assembly protein, and wherein the expression control region affects overexpression of the bacteriophage marker gene encoding the endogenous head assembly protein following infection of *Yersinia pestis*. In one embodiment, the endogenous head assembly protein is the 15.8 kDa ϕA1122 head assembly protein. Other proteins following infection as are known in the art can be used as well, including, head proteins, tail fiber proteins, etc.

In one embodiment, the recombinant bacteriophage marker gene comprises upstream gene ϕ13-LaqI$^q$-pTrc-rbs-gene ϕ13.

In one embodiment, the bacteriophage marker is not surface exposed.

In one embodiment, the bacteriophage marker is not detectable on intact genetically modified bacteriophage by the use of an antibody that specifically binds to the bacteriophage marker.

In one embodiment, the assaying step involves phage lysis.

In one embodiment, the bacteria of the target bacterial type are present in the sample at a concentration of less than about 1000 cells/ml. In other embodiments the bacteria of the target bacterial type are present in the sample at a concentration of less than about 750 cells/ml In further embodiments the bacteria of the target bacterial type are present in the sample at a concentration of less than about 500 cells/ml. In still other embodiments the bacteria of the target bacterial type are present in the sample at a concentration of less than about 250 cells/ml. In still further embodiments the bacteria of the target bacterial type are present in the sample at a concentration of less than about 100 cells/ml.

In one embodiment, the incubation step comprises a period of time less than the time required to initiate a second cycle of infection by progeny of the genetically modified bacteriophage.

In one embodiment, the incubation step comprises a period of time less than the replication time of the genetically modified bacteriophage.

In one embodiment, the incubation step comprises a period of time less than about 45 minutes.

In another embodiment the incubation step comprises a period of time less than about 30 minutes. In further embodiments the incubation step comprises a period of time less than about 20 minutes. In still another embodiment the incubation step comprises a period of time less than about 15 minutes. In still further embodiments the incubation step comprises a period of time less than about 10 minutes. In additional embodiments the incubation step comprises a period of time less than about 5 minutes.

In one embodiment, the period of time from the contacting step to obtaining the result from the assaying step comprises a period of time less about 45 minutes. In another embodiment, the period of time from the contacting step to obtaining the result from the assaying step comprises a period of time less than about 30 minutes. In still another embodiment, the period of time from the contacting step to obtaining the result from the assaying step comprises a period of time less than about 20 minutes. In further embodiments, the period of time from the contacting step to obtaining the result from the assaying step comprises a period of time less than about 15 minutes. In another embodiment, the period of time from the contacting step to obtaining the result from the assaying step comprises a period of time less than about 10 minutes. In another embodiment, the period of time from the contacting step to obtaining the result from the assaying step comprises a period of time less than about 5 minutes.

In one embodiment, the assaying step involves the use of at least one antibody to detect the bacteriophage marker. In another embodiment, the antibody is a monoclonal antibody. In another embodiment, the antibody is present on a lateral flow immunochromatography (LFI) device. In another embodiment, the antibody is present on a SILAS surface.

In one embodiment, the assaying step involves contacting the bacteriophage marker with a first antibody specific for the bacteriophage marker followed by contacting the first antibody-bacteriophage marker complex with a second antibody that is specific for the first antibody or the bacteriophage marker. In one embodiment, the first and second antibodies are the same. In one embodiment, the first and second antibodies are different. In another embodiment, the first antibody is a monoclonal antibody and the second antibody is a polyclonal antibody. In another embodiment, the antibodies are present on a lateral flow immunochromatography (LFI) device.

In one embodiment, the assaying step involves (i) contacting the bacteriophage marker with a first antibody specific for the bacteriophage marker, wherein the first antibody is immobilized on a SILAS surface, (ii) contacting the bacteriophage marker-first antibody complex with a second antibody, wherein the second antibody is specific for the bacteriophage marker or the first antibody and is conjugated to a reactive moiety, and (iii) contacting the first antibody-bacteriophage marker-second antibody complex with a reactant that forms a precipitate in reaction with the reactive moiety of the second antibody, which thereby visibly changes the color of a segment of the SILAS surface. In one embodiment, the first and second antibodies are the same. In one embodiment, the first and second antibodies are different. In another embodiment, the first antibody is a monoclonal antibody and the second antibody is a polyclonal antibody.

In some embodiments of the present disclosure, aptamers are used in place of antibodies as agents capable of specifically binding to a bacteriophage marker.

In some embodiments of the present disclosure, the bacteriophage marker used is a nucleic acid.

In one embodiment, the presence of a bacteriophage marker in an exposed sample induces a color change on a substrate on a detection device of the present disclosure, thereby indicating the presence of target bacteria. In another embodiment, the device comprises a substrate, an immobilization zone on the substrate which includes an immobilization agent designed to immobilize a bacteriophage marker or agent bound thereto, and a color moderator, whereby the presence of the bacteriophage marker or agent bound thereto causes the immobilization zone to change color. In another embodiment, the agent bound thereto is an antibody, for example without limitation a monoclonal antibody. In another embodiment, the immobilization zone comprises antibodies, which antibodies bind specifically to the bacteriophage marker or agent bound thereto. In one embodiment, the color moderator comprises colored beads. In another embodiment, the color moderator comprises a reacting agent and an enzyme which form a precipitate upon reacting. In one embodiment, the detection device comprises a lateral flow strip. In another embodiment, the detection device comprises a SILAS surface.

In one aspect, the present disclosure provides genetically modified bacteriophage selective for a target bacterial type. The genetically modified bacteriophage comprise a recombinant bacteriophage marker gene, which marker gene comprises a nucleic acid sequence encoding a bacteriophage marker operably linked to an expression control region that is capable of affecting expression of the bacteriophage marker gene during the late eclipse or early latent period following infection of bacteria of the target bacterial type.

In one embodiment, the target bacterial type is *Yersinia pestis*. In another embodiment, the target bacterial type is *Bacillus anthracis*. In another embodiment, the target bacterial type is *Francisella* tularensis. In another embodiment, the target bacterial type is *Burkholderia mallei*. In another embodiment, the target bacterial type is *E. coli*. In another embodiment, the target bacterial type is *Staphylococcus*.

In one embodiment, the genetically modified bacteriophage is a genetically modified ϕA1122 capable of infecting *Yersinia pestis*.

In one embodiment, the nucleic acid sequence encoding a bacteriophage marker encodes an endogenous head assembly protein, and the expression control region affects overexpression of the recombinant bacteriophage marker gene encoding the endogenous head assembly protein.

In one embodiment, the nucleic acid sequence encoding a bacteriophage marker encodes a heterologous product, such as without limitation, a heterologous protein, and the expression control region affects expression of the bacteriophage marker gene encoding the heterologous product during the late eclipse or early latent period.

In one embodiment, the nucleic acid sequence encoding a bacteriophage marker encodes a ϕA1122 endogenous head assembly protein, and the expression control region affects overexpression of the bacteriophage marker gene encoding the endogenous head assembly protein following infection of *Yersinia pestis*. In another embodiment, the endogenous head assembly protein is the 15.8 kDa ϕA1122 head assembly protein.

In one embodiment, the recombinant bacteriophage marker gene comprises upstream gene ϕ13-LaqI$^q$-pTrc-rbs-gene ϕ13.

In one aspect, the disclosure provides devices for detecting bacteria of a target bacterial type. In another embodiment, the device is an LFI device. In another embodiment, the device comprises a SILAS surface.

In another embodiment, the detection device is an LFI device comprising a first antibody that specifically binds to a bacteriophage marker, and a second antibody that specifically binds either the bacteriophage marker or the first antibody, wherein the bacteriophage marker is produced during the late eclipse or early latent period following infection of target bacteria by a genetically modified bacteriophage of the disclosure.

In one embodiment, the first antibody binds to an endogenous bacteriophage head assembly protein. In one embodiment, the endogenous bacteriophage head assembly protein is the 15.8 kDa ϕA1122 head assembly protein.

In one embodiment, the detection device comprises a SILAS surface and an antibody that specifically binds to a bacteriophage marker, wherein the bacteriophage marker is produced during the late eclipse or early latent period following infection of target bacteria by a genetically modified bacteriophage of the disclosure.

In one embodiment, the antibody binds to an endogenous bacteriophage head assembly protein.

In one embodiment, the endogenous bacteriophage head assembly protein is the 15.8 kDa ϕA1122 head assembly protein.

In one aspect, the present disclosure provides methods for determining the resistance or susceptibility of a target bacterial type to an antibiotic. The methods comprise the steps of (i) dividing a primary sample containing bacteria of a target bacterial type into a first and a second sample; (ii) adding antibiotic to the first sample alone; (iii) contacting the first and second samples with genetically modified bacteriophage that are selective for the target bacterial type under conditions that allow the genetically modified bacteriophage to infect target bacteria that are present in the second sample and may be present in the first sample, thereby producing first and second bacteriophage exposed samples, wherein the genetically modified bacteriophage comprise a recombinant bacteriophage marker gene comprising a nucleic acid sequence encoding a bacteriophage marker operably linked to an expression control region that affects expression of the bacteriophage marker gene during the late eclipse or early latent period following infection of target bacteria by the genetically modified bacteriophage; (iv) incubating the bacteriophage exposed samples for a period of time sufficient to allow the genetically modified bacteriophage to infect target bacteria present in the second sample; (v) assaying the bacteriophage exposed samples for the bacteriophage marker encoded by the bacteriophage marker gene, wherein the assaying step does not detect the presence of the bacteriophage marker in a bacteriophage exposed sample in the absence of bacterial infection; and (vi) comparing the results of the assaying step for the first and second bacteriophage exposed samples, wherein decreased bacteriophage marker in the first bacteriophage exposed sample compared to the second bacteriophage exposed sample indicates that the target bacterial type is sensitive to the antibiotic.

In one aspect, the disclosure provides kits for determining the presence or absence of bacteria of a target bacterial type in a sample. In one embodiment, the kit comprises a first container comprising a genetically modified bacteriophage capable of infecting the target bacterial type; and a substrate at least a portion of which changes color if the bacteriophage marker is present in the bacteriophage exposed sample. In one embodiment, the kit further comprises a second container containing a buffer solution. In one embodiment, the substrate comprises a lateral flow strip or a SILAS surface. In one embodiment, the first container includes a dropper designed to release drops of a predetermined size.

In one aspect, the disclosure provides methods for detecting a plurality of bacterial types of interest simultaneously. In one embodiment, the methods involve the use of a plurality of distinct genetically modified bacteriophage specific for each type of bacteria. In one embodiment, the distinct genetically modified bacteriophage comprise distinct bacteriophage marker genes. In one embodiment, the plurality of distinct genetically modified bacteriophage are added to the same sample.

BRIEF DESCRIPTION OF THE DRAWINGS

FIG. 1 shows PCR amplification primers and conditions for amplification of upstream gene ϕ13, $LaqI^q$, pTrc-rbs, and gene ϕ13.

FIG. 5 shows the sequence of the 15.8 kDa ϕA1122 head assembly protein.

DETAILED DESCRIPTION

Figure 2:
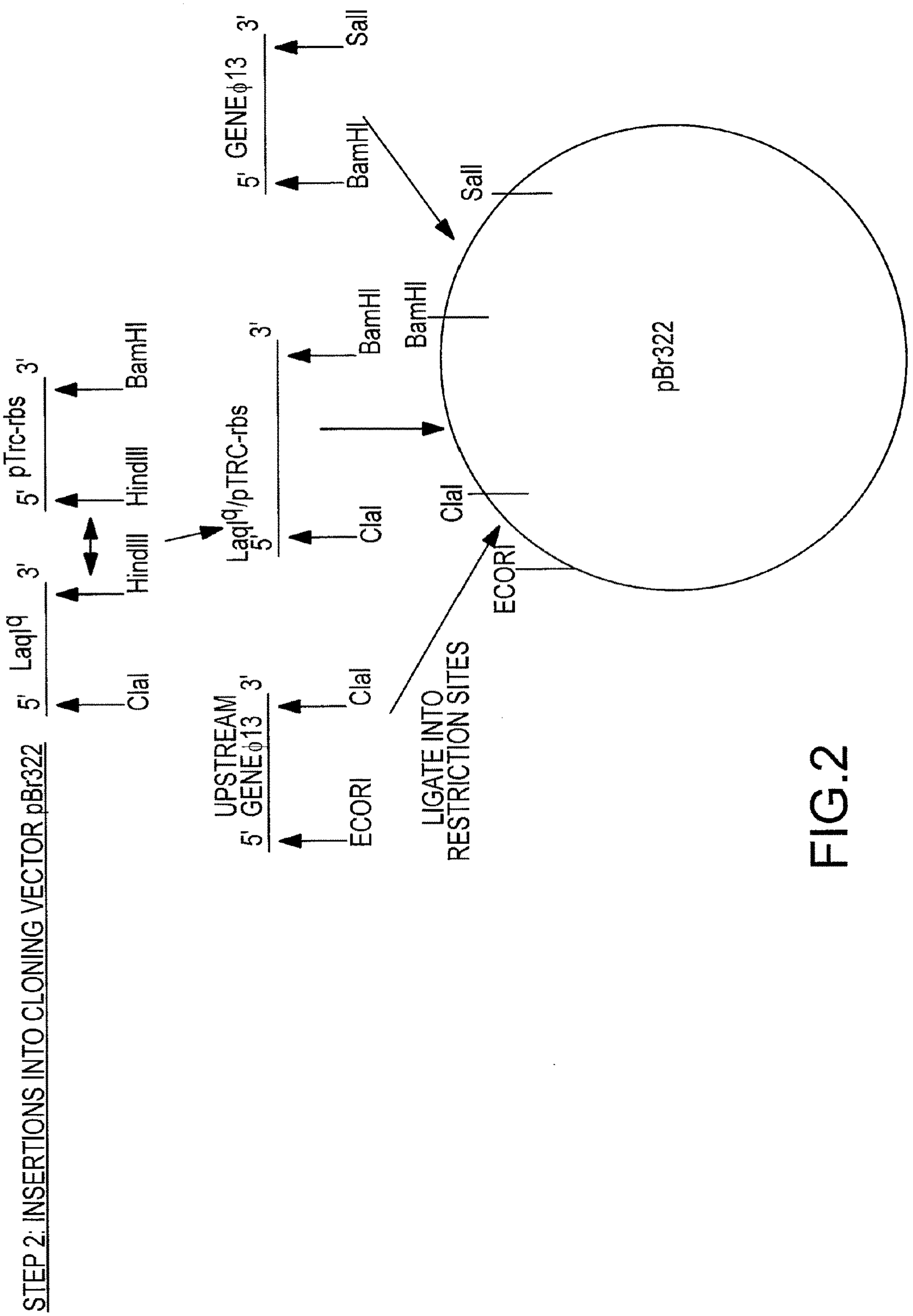
FIG. 2 shows cloning strategy for assembling a construct comprising upstream gene ϕ13, $LaqI^q$, pTrc-rbs, and gene ϕ13.

The present disclosure relies on the use of genetically modified bacteriophage to detect the presence of bacteria of a target bacterial type in a sample, and exploits the highly specific phage-bacterial infection to provide a bacterial detection method which is highly specific to target bacteria, very sensitive and fast. Following incubation of genetically modified bacteriophage with a sample, the exposed sample is assayed for the product of a recombinant bacteriophage marker gene, referred to herein as the bacteriophage marker, in order to assess whether bacterial infection has occurred and, accordingly, whether target bacteria are present in the sample. The bacteriophage marker may be detected by any suitable means, including but not limited to detection through the use of lateral flow strips, a SILAS surface, or a MALDI mass spectrometer.

A highlight of the present disclosure is that complete bacteriophage replication, the production of progeny bacteriophage, and multiple rounds of bacterial infection are not required to achieve adequate amplification and production of a detectable signal. Rather, the genetically modified bacteriophage of the disclosure are engineered to express a recombinant bacteriophage marker gene at levels sufficient to allow detection after a single infection. Further, the recombinant bacteriophage marker gene is engineered to be expressed very early following infection, particularly during the late eclipse or early latent period. Both of these qualities significantly reduce the lag time to detection of target bacteria in a sample, a feature highly desirable in devices and methods used to detect pathogenic bacteria.

Methods for Detecting Target Bacteria

In one aspect, the disclosure provides methods for determining the presence or absence of a bacteria of a target bacterial type in a sample.

In a embodiment, the target bacterial type is *Yersinia pestis*. In another embodiment, the target bacterial type is *Bacillus anthracis*. In another embodiment, the target bacterial type is *Francisella* tularensis. In another embodiment, the target bacterial type is *Burkholderia mallei*. In another embodiment, the target bacterial type is *E. coli*. In another embodiment, the target bacterial type is *Staphylococcus*.

The methods comprise combining genetically modified bacteriophage of the disclosure with a sample to be tested for the presence of target bacteria, to form a bacteriophage exposed sample. In another embodiment, the bacteriophage, may be in a suspension or solution, and may be added in a predetermined concentration to the sample. The object of the method is to detect a specific bacterial type, i.e., the "target bacterial type", and a correspondingly specific genetically modified bacteriophage is used. For example, a genetically modified ϕA1122 capable of infecting *Yersinia pestis* can be used to specifically detect *Yersinia pestis*.

To detect multiple target bacterial types, one species of bacteriophage specific to each target bacterial type may be added to a single test sample, or individually to divisions thereof. For the purposes of simplicity, the method will be described henceforth as it applies to detecting a single target bacterial type.

A sample is generally in a liquid form but can be a solid or a powder. The sample can be a mixture or suspension containing many different organic and inorganic compounds. It may be pretreated in a variety of ways to prepare it for testing. For example, the sample may be purified or filtered to remove unwanted components or to concentrate bacteria. It may be cultured in a media conducive to the incubation of the target bacteria or to induce the target bacteria into a more viable state. The sample may be in a relatively untreated state such as might be the case with a sputum, blood, or water sample.

The bacteriophage itself may be added to the sample in a variety of forms. It may be added in a dry state. The bacteriophage may be mixed or suspended into a liquid reagent mixture. It may be suspended in a vial to which the sample is added. It also may take any other suitable form. The bacteriophage added to the sample is sometimes herein referred to as "the parent phage". Once contacted with bacteriophage, the sample is referred to as a bacteriophage exposed sample.

The bacteriophage exposed sample may be incubated for a predetermined time. Incubation may be for a sufficient time to allow production of the bacteriophage marker in infected target bacteria if present in the exposed sample. The bacteriophage exposed sample is in a condition that is conducive to phage infection of the target bacteria. This can be accomplished in a variety of ways well known to those skilled in the art. For example, the parent phage may be mixed into a reagent that, when added to the sample, results in a test sample conducive to infection. The sample may be prepared in many different ways to establish conditions conducive to phage infection.

Assuming there were target bacteria in the sample, the test sample will contain a bacteriophage marker. The parent phage infects the target bacteria by attaching themselves to cell walls of the target bacteria and injecting the viral nucleic acid to create infected bacteria. The recombinant bacteriophage marker gene is then abundantly expressed in the infected bacteria. In one embodiment, the method involves lysing bacteria. In one embodiment, a microbial lysozyme is added to the bacteriophage exposed sample. In one embodiment, lysing involves adding chloroform to the bacteriophage exposed sample, treating the bacteriophage exposed sample with acid, or otherwise physically processing the bacteriophage exposed sample.

Importantly, in contrast to other methods, production of progeny phage, rupturing of the host, release of progeny phage into the test sample and subsequent rounds of bacterial infection are not required in the present disclosure. Moreover, while many prior art methods rely on detecting intact progeny phage, a highly embodiment of the present disclosure involves the detection of an overexpressed head assembly protein, which is not accessible for detection on intact progeny phage. In a less embodiment of the disclosure, wherein progeny phage are produced, the methods involve lysing progeny phage to expose the product of a recombinant bacteriophage marker gene.

The bacteriophage marker is an indirect indicator of the presence of target bacteria in the sample. Where the bacteriophage marker is a component of parent phage, the initial concentration of parent phage in the exposed sample may be controlled such that the background signal produced is undetectable in the assay. Thus, if no target bacteria are present in the sample, no infection occurs, no recombinant bacteriophage marker gene is expressed, and no new bacteriophage marker is synthesized. In one embodiment, a negative control is run using a control sample that is known to lack the target bacterial type in order to confirm that the bacteriophage used does not produce a background signal in the assay. Other aspects of the disclosure may provide for use of a negative control to identify a background signal that is distinguishable from any signal arising from an exposed sample comprising target bacteria. Thus, in another embodiment of the disclosure, the assaying step is capable of detecting bacteriophage marker in the absence of bacterial infection, but the signal is distinguishable from that produced following bacterial infection.

Methods for detecting bacteriophage include ELISA (Kofitsyo S. Cudjoe, Therese Hagtvedt, and Richard Dainty, "Immunomagnetic Separation of *Salmonella* From Foods And Their Detection Using Immunomagnetic Particle", International Journal of Food Microbiology, 27 (1995), pp. 11-25), dot blot assay (Eystein Skjerve, Liv Marit Rorvik, and Orjan Olsvick, "Detection Of *Listeria Monocytogenes* In Foods By Immunomagnetic Separationt1A, pplied and Environmental Microbiology, November 1990, pp. 3478-3 48 I), electrochemiluminescence (Hao Yu and John G. Bruno, Immunomagnetic-Electrochemiluminescent Detection Of *Escherichia coli* 0157 and *Salmonella typhimurium* In Foods and Environmental Water Samples", Applied and Environmental Microbiology, February 1996, pp. 587-592), and flow cytometry (Barry H. Pyle, Susan C. Broadway, and Gordon A. McFeters, "Sensitive Detection of *Escherichia coli* 0157:H7 In Food and Water By Immunomagnetic Separation And Solid-Phase Laser Cytometry", Applied and Environmental Microbiology, May 1999, pp. 1966-1972). Although these tests provide satisfactory results, they are laborious to perform and give binary responses (yes/no) that are highly susceptible to false-positive results due to cross-reactivity with non-target analytes. Another method for detecting analyte is matrixassisted laser desorption~ionization (M ALDI) time-of-flight (TOF) mass spectrometry (MS) (Holland et al., 1996; van Barr, 2000; Madonna et al., 2000). Electrospray ionization (ESI) may also be used.

In various embodiments, the assay step may involve immunochemistry, for example without limitation, ELISA, radio immuno assay (RIA), lateral flow immunochromatography. In other embodiments, the assay step may involve mass spectrometry (MS) and/or ionization, for example without limitation, MALDI-TOF/MS, Liquid Chromatography (LC)-MS, and electrospray ionization (ESI)-MS.

Any detection method or apparatus that detects the bacteriophage marker will suffice for the method. methods are immunoassay methods utilizing antibody-binding events to produce detectable signals including ELISA, flow cytometry, western blots, aptamer-based assays, radioimmunoassay, immunoflouresence, and lateral flow immunochromatography (LFI). Other methods are matrix-assisted laser desorption/ionization with time-of-flight mass spectrometry (MALDI-TOF-MS), sometimes referred to herein as MALDI, and the use of a SILAS surface which changes color as a detection indicator. Also contemplated are PCR, genetic probe biosensors, photoaptamers, molecular beacons, and gel electrophoresis. Other aspects of the disclosure are methods that are adaptable to portable devices, such as without limitation, LFI. Assays may be done using a detection device of the present disclosure.

In another embodiment, wherein progeny phage are produced, phage dissociation may be done. Phage dissociation may comprise adding a phage dissociation agent to the exposed sample. The phage dissociation agent breaks up the phage particles into their constituent components including individual capsid proteins and viral nucleic acids. Examples of phage dissociation agents are acid treatments, urea, denaturing agents, and enzymes. Any suitable phage dissociation agent may be used.

In one embodiment, the bacteriophage marker is a component of parent phage, and the concentration of parent phage in the exposed sample is kept below the background detection limit. The potentially low concentration of parent phage may result in conditions where the ratio of parent phage to target bacteria in the exposed sample is less than 1; i.e., the Multiplicity Of Infection (MOI) is low. To ensure that all target bacteria in the test sample have a high probability of being infected, the incubation time can be made be made longer, for example, a time period greater than that from time of infection to late eclipse or early latent period. It may be beneficial that the parent bacteriophage do not obfuscate the bacteriophage marker signal that follows from infection of target bacteria when a higher MOI, e.g., MOIs greater than 1, such as, without limiting, greater than 5, are used.

In one embodiment, parent phage may be tagged and removed from an exposed sample to reduce background. See, for example, US 2005/0003346.

Screening Methods

In one aspect, the disclosure provides methods for detecting the susceptibility or resistance of a target bacterial type to an agent. Susceptibility to an agent means target bacteria growth and/or survival is sensitive to the agent. The agent may be an antibiotic.

A sample containing the target bacteria is divided into two, a first sample and a second sample. A first agent, for example without limitation, an antibiotic, is added to the first sample whereupon the target bacteria in the first sample exhibit reduced growth and/or survival if they are not resistant to the first agent. The first and second samples are exposed to genetically modified bacteriophage appropriate to the target bacterial type. Following incubation, the first and second exposed samples are assayed for the bacteriophage marker, and results from the first and second samples are compared. A reduction in bacteriophage marker in the first exposed sample (i.e., the one receiving agent) as compared to the second exposed sample indicates that the target bacteria are sensitive to the agent.

To screen for resistance to any one of a range of agents simultaneously, all of the agents of interest may be added to the first sample. This comparative process can also be used to test whether a bacterial decontamination process has been successful. By dividing a sample into a control portion and a test portion, the effectiveness of bacteriological methods and materials can be tested. Those skilled in the art will recognize that the processes of the disclosure can be used in nearly every instance where it is desirable to determine if live bacteria are present.

Construction of Genetically Modified Bacteriophage

In one aspect, the disclosure provides genetically modified bacteriophage capable of infecting bacteria of a target bacterial type, and methods of making the same.

The genetic manipulation of bacteriophage is well known in the art. Regarding bacteriophage, the use thereof as cloning vectors, and the generation of genetically modified bacteriophage, see, for example, Ausubel et al., *Current Protocols in Molecular Biology*, Section III Vectors Derived from Lambda and Related Bacteriophages, ISBN: 978-0-471-50338-5. Regarding ϕA1122, see for example, Garcia et al., J. Bacteriol. 2003 September; 185(17):5248-62.

The genetically modified bacteriophage of the disclosure comprise a recombinant bacteriophage marker gene. A recombinant bacteriophage marker gene comprises a nucleic acid sequence encoding a bacteriophage marker operably linked to an expression control region that affects expression of the recombinant bacteriophage marker gene during the late eclipse or early latent period following infection of target bacteria.

In one embodiment, the recombinant bacteriophage marker gene encodes an endogenous bacteriophage product. In another embodiment, the endogenous bacteriophage product is a head assembly protein. In another embodiment, the bacteriophage is a genetically modified ϕA1122 comprising recombinant bacteriophage marker gene encoding a ϕA1122 head assembly protein, such as without wishing to be limited, the 15.8 kDa head assembly protein, and the expression control region is modified compared to the endogenous head assembly protein gene and affects over-expression of the head assembly protein gene following infection of *Yersinia pestis.*

In one embodiment, the recombinant bacteriophage marker gene encodes a heterologous product, such as without wishing to be limited, a heterologous protein, and the expression control region affects expression of the heterologous product during the late eclipse or early latent stage following infection of the corresponding bacterial type.

In one embodiment, a recombinant bacteriophage marker gene replaces a portion or all of an endogenous bacteriophage gene in a genetically modified bacteriophage. Owing to the fact that the present disclosure does not require production of progeny phage for signal detection, endogenous genes essential to phage replication and progeny phage formation may be deleted or replaced, and parent phage may be produced by providing such factors in trans.

In one embodiment, targeted insertion of a recombinant bacteriophage marker gene into a bacteriophage genome is done. Such insertion may be done using standard enzymatic processes, e.g., enzymatic digestion and ligation processes, or may be done using homologous recombination, or by other means known for targeted insertion. In a embodiment, a recombinant bacteriophage marker gene is inserted into a head assembly protein gene locus in a bacteriophage genome.

In one embodiment, the bacteriophage is selected from the group of bacteriophage capable of infecting *Yersinia pestis, Bacillus anthracis, Francisella tularensis, Burkholderia mallei, E. coli*, or *Staphylococcus.*

Detection Devices

In one aspect, the disclosure provides devices useful for the detection of target bacteria by way of the detection of a bacteriophage marker.

In one embodiment, the disclosure provides LFI devices useful for the detection of a bacteriophage marker. A lateral flow strip may include a sample application pad, a conjugate pad, a substrate in which a detection line and optionally an internal control line are formed, and an absorbent pad, all mounted on a backing, for example without limitation, a plastic backing. See, for example, U.S. 2005/0003346. The substrate may be a porous mesh or membrane. The conjugate pad may contain colored beads each of which has been conjugated to a first antibody, forming first antibody-bead conjugates. In one embodiment, the first antibody selectively binds to the bacteriophage marker in the exposed sample. In one embodiment, a detection line and a control line are both reagent lines and each form an immobilization zone; that is, they contain a material that interacts in an appropriate way with the bacteriophage marker or the first antibody attached thereto. In one embodiment, the interaction is one that immobilizes the bacteriophage marker. A detection line may comprise immobilized second antibodies, with antibody line perpendicular to the direction of flow along the strip, and being dense enough to capture a significant portion of the bacteriophage marker. In one embodiment, the second antibody binds to the first antibody. In one embodiment, the second antibody binds to the bacteriophage marker. In one embodiment, the second antibody and the first antibody are identical. In another embodiment, the second antibody and the first antibody are distinct. In one embodiment, the first antibody is a monoclonal antibody. Optionally, the strip may include a second reagent line, optionally including a third antibody. The third antibody may or may not be identical to one or more of the first and second antibodies. The second reagent line may serve as an internal control zone to test if the assay functioned properly.

In one embodiment, one or more drops of an exposed sample may be added to the sample pad. The exposed sample flows along the lateral flow strip toward the absorbent pad at the opposite end of the strip. As the bacteriophage marker molecules, if present, flow along the conjugate pad toward the membrane, they pick up one or more of the first antibody-bead conjugates forming marker-bead complexes. As the marker-bead complexes move over second antibodies they form an immobilized and concentrated marker-bead-second antibody complex. If enough marker-bead complexes bind to the row of immobilized second antibodies, a colored line becomes visible to the naked eye. A visible line indicates that the target bacteria were present in the sample. If no line is formed, then target bacteria were not present in the sample or were present in concentrations too low to be detected with the lateral flow strip. In some aspects of the disclosure, the parent phage alone do not produce a visible line on the lateral flow strip. The antibody-bead conjugates are color moderators that are designed to interact with the bacteriophage marker. When they are immobilized in the immobilization zone, they cause the immobilization zone to change color.

In one embodiment, a device comprising a SILAS surface is used for detection of a bacteriophage marker. A SILAS surface comprises a semiconducting or insulating wafer having an optical coating covered with an attachment polymer. As known in the art, the SILAS surface is designed to reflect specific wavelengths of light and to attenuate others by interference. These surfaces generate a visible signal by the direct interaction of light with the thin films formed on the surface. The thin films include optical coatings and/or biological films created by binding of specific target molecules to the surface. A positive result is usually seen as a color change from gold to purple because the optical path of the light is lengthened by the accumulated biological mass on the surface. The thickness and refractive index of the film determines the particular colors and shades that are observed. Generally, wavelengths of light which reflect from the surface in phase with the incoming light will be additive, or undergo constructive interference, and thus be visible. Wavelengths that reflect from the surface out of phase with the incoming light will be attenuated through destructive interference and will not emerge from the films. In some aspects, the wafer comprises silicon, the optical coating comprises silicon nitride, and the attachment polymer comprises a hydrophobic polymer. The SILAS surface may be used indicate the presence of a bacteriophage marker. In one embodiment, a first antibody specific to the bacteriophage marker is attached to the attachment polymer, the surface of which becomes an immobilization zone. An exposed sample is contacted to the surface. If the bacteriophage marker is present, it attaches to the first antibody. A second detector antibody may be contacted to the surface and attaches to the bacteriophage marker or the first antibody. The second antibody is labeled with a reacting agent, such as horseradish peroxidase (HRP) or alkaline phosphatase. Then an enzyme, such as 3,3',5,5' tetramethylbenzidine (TMB), is applied to the surface which reacts with the HRP to form a precipitant which forms a thin film layer which alters the color of the surface. Thus, the presence of the bacteriophage marker causes the immobilization zone to change color. SILAS surfaces are available from Thermo Electron Corporation, 81 Wyman Street, Waltham, Mass. 02454-9046. For more details, see, for example, U.S. 2005/0003346.

Kits

In one aspect, the disclosure provides kits useful for the detection of target bacterial types in a sample.

In one embodiment, a kit includes a container of buffer solution, a reaction container, and one or more detection elements. Kits of the present disclosure may also include packaging materials, directions for use, information pamphlets, receptacles for holding test kit parts, protective casing, etc. Reference detection elements indicating the expected result if no target bacteria are present may also be included. For example, if the detection element is a lateral flow strip, the reference detection element may be an identical lateral flow strip on which a reference exposed sample has been applied wherein the sample had no target bacteria present. The reaction container may include a container body and a container closure. In one embodiment, the reaction container body is a bottle and the reaction container closure is a bottle cap. The reaction container contains genetically modified bacteriophage. In another embodiment, a predetermined amount of genetically modified bacteriophage is attached to the interior wall of the reaction container body. The cap may be a screw-on cap having interior threads that mate with threads on the top portion of bottle. The cap may include a dispenser, which may be a dropper head designed to release drops of a predetermined size. In another embodiment, the detection element is a lateral flow strip, but it also could be a SILAS surface element.

In one embodiment, the kit is used as follows. The reaction bottle is decanted by removing the cap and the dropper head and adding a volume, e.g., about 5 milliliters, of sample. Then the buffer solution is added. The dropper head and cap are replaced on the bottle, and the capped reaction container is shaken, in some aspects for a prescribed amount of time, such as without limitation, one minute, and the solution is then incubated by allowing it to sit for another prescribed amount of time, such as without limitation, ten minutes. The cap is then removed and a prescribed amount of the incubated sample is released onto the sample pad. The user then waits for, in some aspects a predetermined amount of time, such as without limitation, three minutes. The user looks in the detection window for the results. In a embodiment, a first color, such as blue, appears if the sample contains the bacterial type for which the test kit is specified. If no line of the first color appears, the test is negative. Optionally, a second line, which may be of a second color, appears to indicate that the test is valid. If a reference detection element is used, then the test line may be compared to the reference line to determine if the test is positive or negative.

EXPERIMENTAL

Example 1

Detection of ϕA1122 Head Assembly Protein

Phage semi-purification and purification: A modified procedure of that used by Sambrook et al., (Molecular Cloning: A Laboratory Manual. 1989: Cold Spring Harbor Laboratory Press) for polyethylene glycol (PEG) precipitation and cesium chloride (CsCl) gradient purification of phage samples was used. To 500 mL of 0.22 micron filtered phage stock 50 g of PEG 8000 (10% w/v) and 30 g of NaCl were dissolved at room temperature with stirring or shaking. The sodium chloride was added to promote the dissociation of phage particles from any nucleic acids remaining in solution. The mixture was then iced for no less than one hour or refrigerated overnight to precipitate the phage particles. Precipitated phage were pelletized by centrifugation (11,000×g for 15 min at 4° C.) and resuspended in 8 mL of 0.85% normal saline solution. An equal amount of chloroform was added and the solution was vortexed for 30 seconds and centrifuged at 4,000×g for 15 minutes at 4° C. The aqueous phase (top layer) containing phage particles was collected and considered as semi-purified. To obtain a purified preparation, PEG-precipitated phage samples were subjected to a CsCl equilibrium gradient. To a 35 mL polyallomar tube containing 5-7 mL of phage, a 4 step CsCl:TE gradient was prepared and underlaid in the following order: 1:2; 1:1, 2:1, 1:0. The gradients were ultracentrifuged for 24 hours at 25,000 rpm using a SW-28 rotor and LM-8 Beckman Ultracentrifuge. Purified phage bands were collected above the 2:1 layer, dialyzed against 0.85% saline and 0.2 μm filter sterilized before analysis by MALDI-MS.

MALDI preparation: Ferulic acid (15 mg/mL) in a 17:33:50 mixture of 88% formic acid, acetonitrile and de-ionized water solution was utilized as the matrix (see Madonna et al., Rap. Commun. Mass Spectrom, 2000. 14: p. 2220.) Mass spectra were obtained with a 337 nm N2 laser in linear mode using a PerSeptive Biosystems Voyager-DE STR+MALDI-TOF-MS (Applied Biosystems, Inc. Framingham Mass., USA). Samples were applied to a hydrophobic target plate using the dried droplet method in a sandwich fashion as follows: 0.5 μL of matrix: 0.5 μL of sample: 0.5 μL of matrix. The following parameters were used to collect spectra: accelerating voltage 25 kV; grid voltage 75%; delayed extraction time of 100 ns; and 2 kDa low mass ion gate. Mass spectra were acquired as an average of 150 laser shots taken from 3 replicate sample spots (50 shots per spectrum). Raw data from Data Explorer (Applied Biosystems, Inc. Framingham, Mass., USA) was exported into SigmaPlot 7.0 (Point Richmond, Calif. USA) for spectral comparison.

Figure 4A:
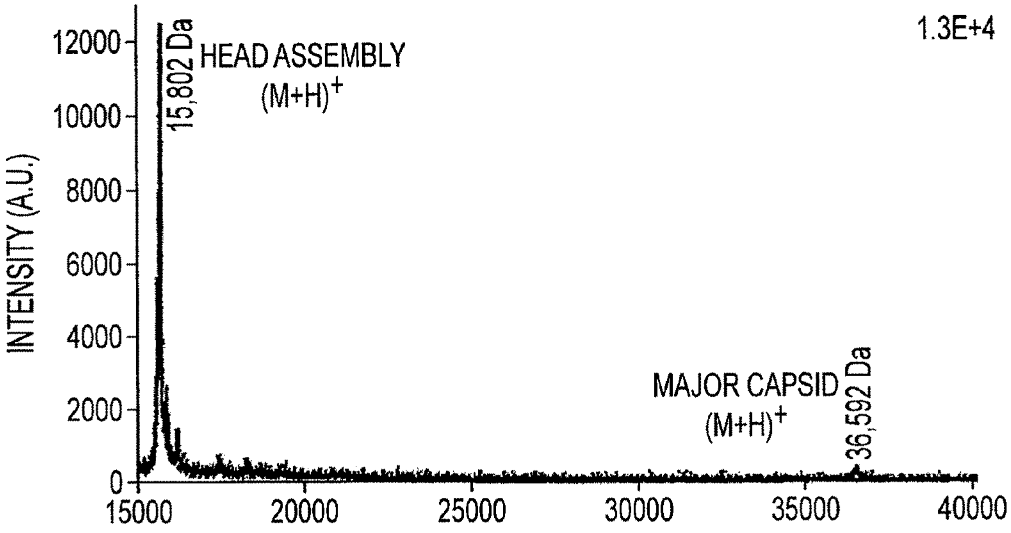
FIG. 4 shows an exemplary MALDI spectrum, sample preparation 1 hour post infection of *Yersinia pestis* by ϕA1122, revealing head assembly protein signal at 15.8 kDa.
Figure 4B:
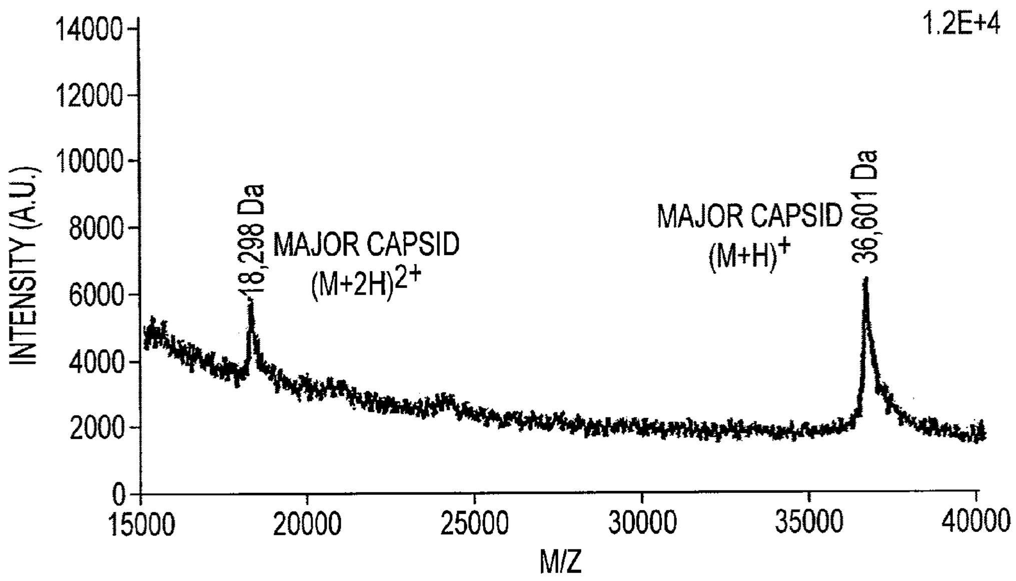

Results: The MALDI-MS spectral profile comparison for phage ϕA1122 is shown for the semi-purified preparation in FIG. 4A and the purified preparation in FIG. 4B. The singly charged major capsid protein is obtained at a mass of 36.6 kDa in both spectra correlating extremely well to the calculated sequenced mass of the major capsid protein for this phage. The gradient-purified preparation clearly shows the presence of a doubly charged capsid protein at a mass of 18.3 kDa. The signal intensity is consistently stronger for the capsid protein in the gradient purified preparation than the semi-purified preparation. Interestingly, the singly charged capsid protein and its doubly charged species almost disappear relative to a large ionizing signal obtained at 15.8 kDa in the semi-purified phage preparation (FIG. 4A), while the purified phage spectrum clearly lacks the 15.8 kDa signal. The absence of the 15.8 kDa signal in the purified MALDI-MS spectrum suggests that the head assembly protein becomes internalized or degraded upon completion of assembling a fully mature capsid. The assembly of an icosahedral capsid is known to be constructed around the head to tail connector via formation of a procapsid or inner shell. A scaffolding or assembly protein, like the head assembly protein of phage ϕA1122, is not only required in the construction of a procapsid, but also for nucleation of the coat proteins about the inner shell to form a fully mature phage. Assembly proteins are typically not found as part of mature phage and may be internalized as the assembly of mature capsid proceeds via nucleation of ~415 capsid proteins on the outside and assembly proteins on the inside of the inner shell, shielding them from ionization. Evidence supporting this is obtained from TEM micrographs of the two different ϕA1122 phage preparations (data not shown). A micrograph of the semi-purified preparation shows a high concentration of apparent intermediate sized procapsid structures, while the micrograph of the purified phage preparation lacks these small structures. The 15.8 kDa biomarker corresponds to the phage head assembly protein, the sequence of which is given in FIG. 5.

Example 2

Expression of 15.8 kDa ϕA1122 Head Assembly Protein Following Infection

Bacteriophage amplification: After determining the ϕA1122 phage MALDI-MS detection limit of to be 2(±2)×$10^8$ pfu/mL, amplification experiments were performed with initial bacterial densities ranging from 1×$10^8$ to 1×$10^5$ cfu/mL which were infected with 3(±2)×$10^6$ pfu/mL of ϕA1122 phage. One mL of bacteria samples were infected with 100 μL of phage and incubated with shaking (150 rpm/min) at 28° C. for 1-3 hours. Sample clean-up prior to MALDI analysis consisted of pelletizing bacterial debris (10,000×g for 5 minutes), followed by filtration through a standard 0.22 μm cellulose acetate membrane. Samples were polyethylene glycol (PEG) precipitated and re-suspended in an equal volume of 0.85% saline solution. To remove the PEG, differential centrifugation (11,000×g for 15 min) was employed with an equal amount of chloroform. The aqueous phase (top layer) containing phage particles were collected and considered semi-purified for MALDI-MS analysis.

MALDI-MS: Ferulic acid (15 mg/mL) in a 17:33:50 mixture of 88% formic acid: acetonitrile: de-ionized water was utilized as the matrix (see Madonna et al., supra). Mass spectra were obtained with a 337 nm N2 laser in linear mode using a PerSeptive Biosystems Voyager-DE STR+MALDI-TOF-MS, (Applied Biosystems, Inc., Framingham, Mass., USA). Samples were applied to the hydrophobic target plate in a sandwich fashion as follows: 0.5 μL of matrix: 0.5 μL of sample: 0.5 μL of matrix. The following parameters were used to collect spectra: accelerating voltage 25 kV; grid voltage 80%; delayed extraction time 100 ns; and a to 2 kDa low mass ion gate. Mass spectra were acquired as an average of 150 laser shots taken from 3 replicate sample spots (50 shots per spectrum). Raw data from Data Explorer (Applied Biosystems, Inc. Framingham, Mass., USA) was exported into SigmaPlot 7.0 (Point Richmond, Calif. USA) for spectral comparison.

Figure 6:
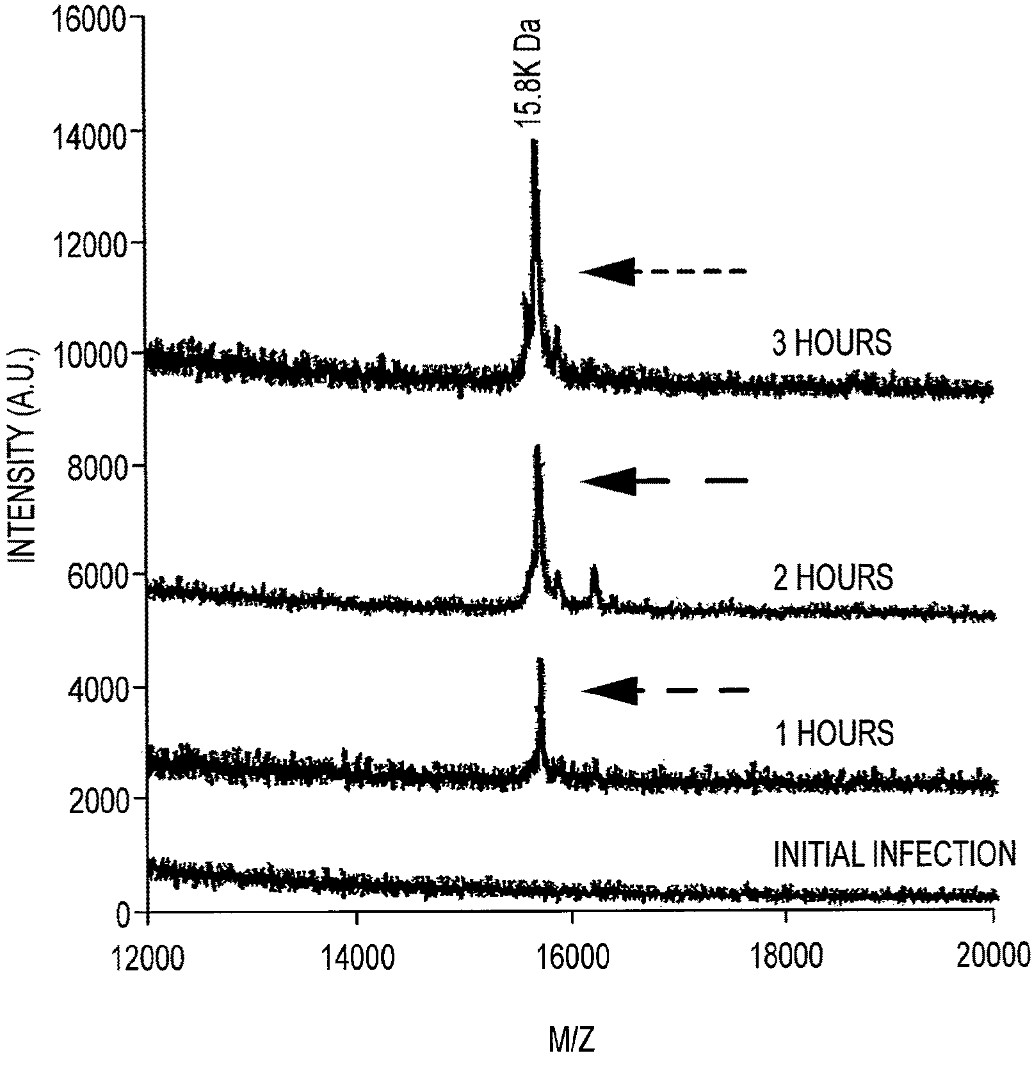
FIG. 6. MALDI spectra for conditions as indicated, showing production of endogenous head assembly protein following infection of bacteria with wildtype ϕA1122. 3 hour amplification experiments with initial bacterial concentration of $10^8$ cells/mL. MOI=0.003. MALDI-MS spectra of ϕA1122 phage amplified in *Y. pestis* cells in the mass range of 12-20 kDa.
Figure 7:
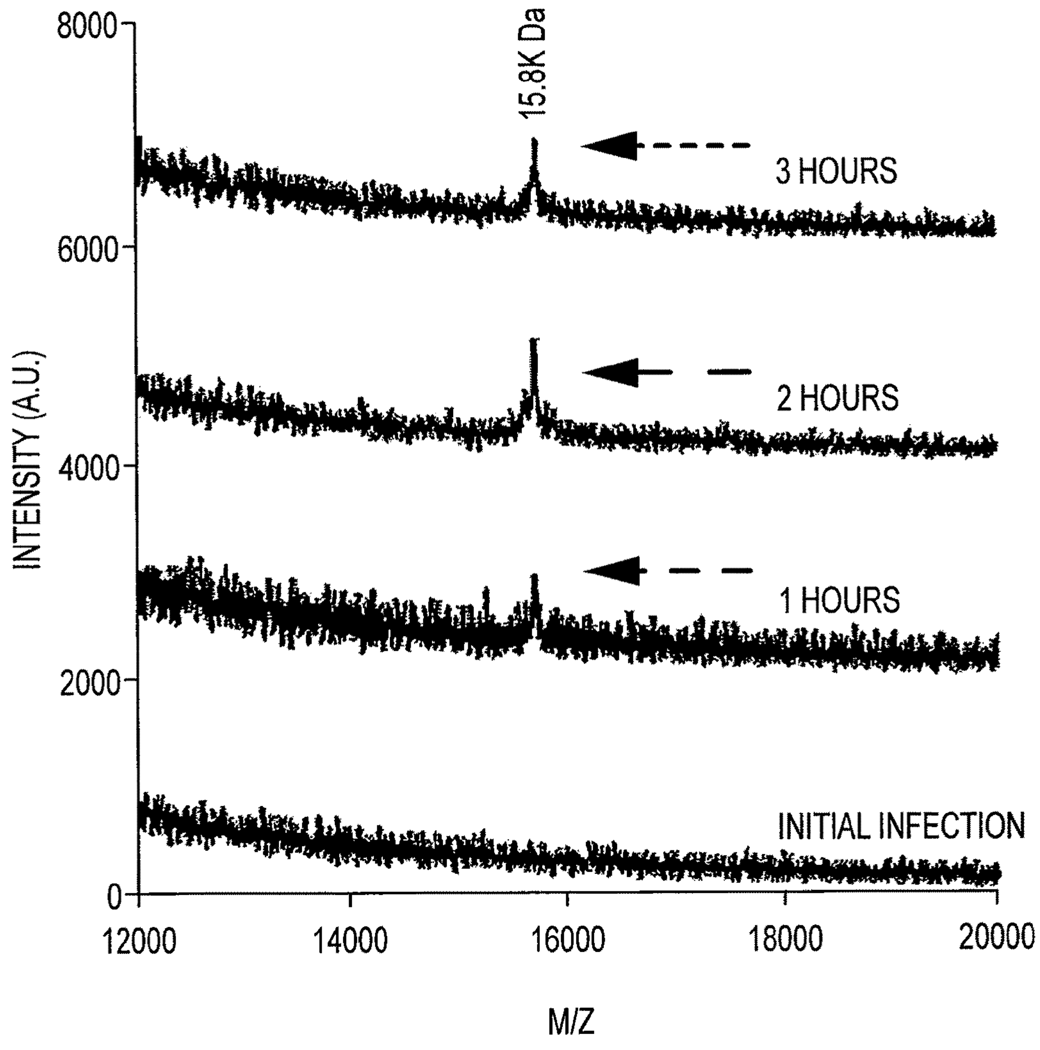
FIG. 7. MALDI spectra for conditions as indicated, showing production of endogenous head assembly protein following infection of bacteria with wildtype ϕA1122. 3 hour amplification experiments with initial bacterial concentration of $10^7$ cells/ml. MOI=0.03. MALDI-MS spectra of ϕA1122 phage amplified in *Y. pestis* cells in the mass range of 12-20 kDa.

Results: MALDI-MS spectra from the actual 3-hour phage amplification experiments for the different bacterial densities are presented in FIGS. 6-8. For all three densities, initial infection is shown in the bottom spectrum in each Figure and indicates no detectable ϕA1122 phage signal when an infecting phage concentration of phage of 3×$10^6$ pfu/mL was utilized. The culture was deliberately infected well below the detectable threshold (LOD=2×$10^8$ pfu/mL) of MALDI-MS so that any detectable change is the result of progeny phage from the amplification event. FIGS. 6 and 7 demonstrate that at bacterial densities of $10^8$ and $10^7$ cfu/mL a detectable phage signal is apparent at 1-hour post infection. Subsequent sampling at these densities 2 and 3-hours post infection show increased signal intensities.

Figure 8:
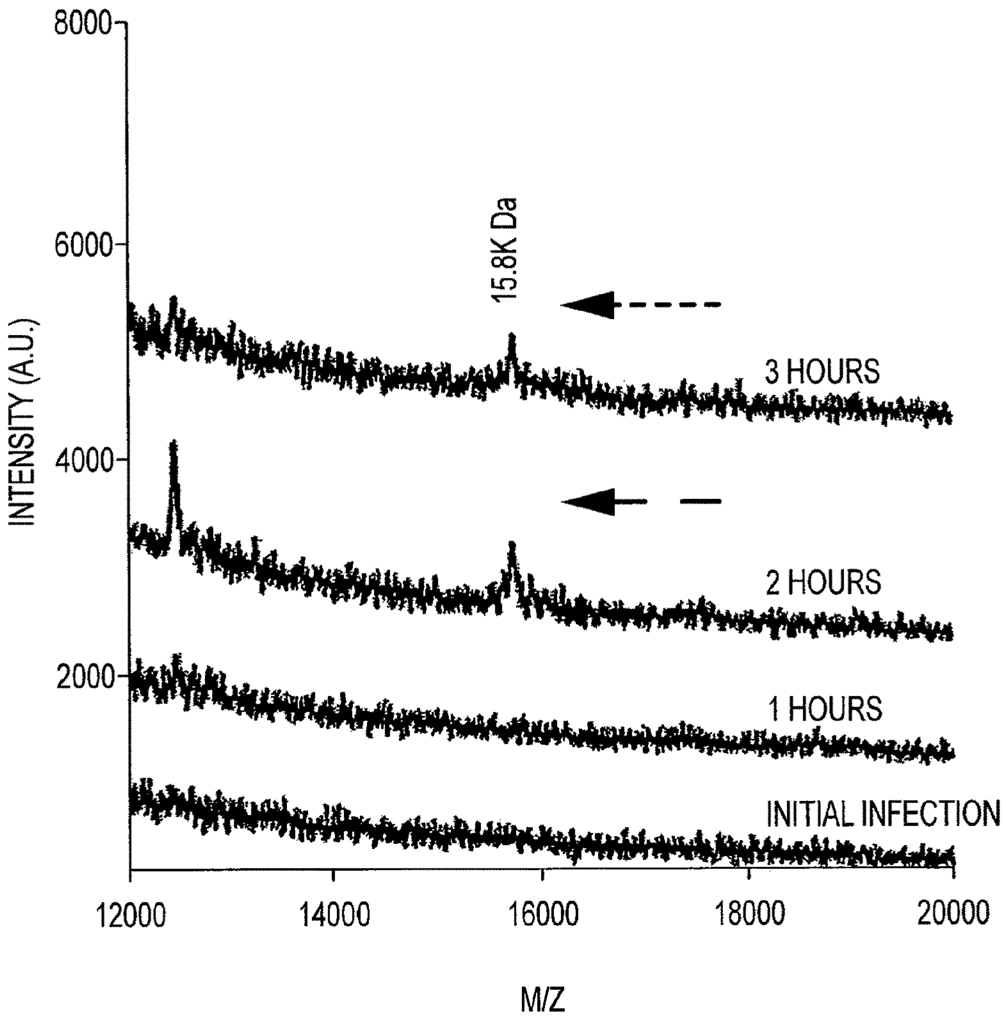
FIG. 8. MALDI spectra for conditions as indicated, showing production of endogenous head assembly protein following infection of bacteria with wildtype ϕA1122. 3 hour amplification experiments with initial bacterial concentration of $10^6$ cells/ml. MOI=0.3. MALDI-MS spectra of ϕA1122 phage amplified in *Y. pestis* cells in the mass range of 12-20 kDa.
Figure 9:
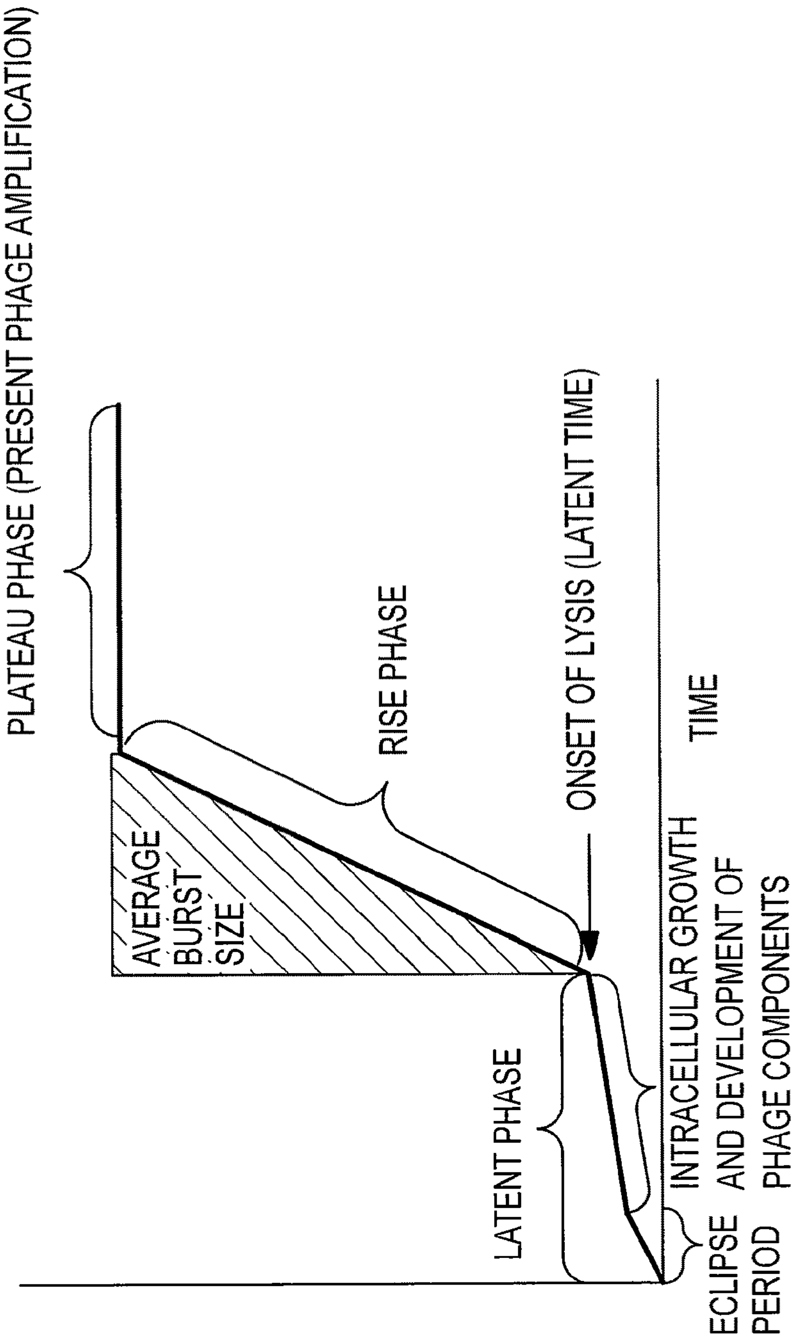
FIG. 9. Graph showing the time course of ϕA1122 infection of *Yersinia pestis*. The 15.8 kDa endogenous head assembly protein is produced during the late eclipse/early latent period.

FIG. 8 demonstrates that as the bacterial concentration is decreased to $10^6$ cfu/mL a MALDI-MS signal is not apparent until 2 hours post-infection. When the bacterial concentration was decreased another order of magnitude, no apparent MALDI-MS signal was obtained at $10^5$ cfu/mL after 3-hours post infection when an MOI of 3.0 was utilized.

Antibiotic Resistance

The sensitivity of *Yersinia pestis* to a test agent is determined by using genetically modified bacteriophage ϕA1122 which overexpresses the 15.8 kDa head assembly protein during the late eclipse or early latent period following infection of *Yersinia pestis*. A sample comprising *Yersinia pestis* at a concentration of 250 cells/ml is divided into two samples, A and B. Sample A is contacted with the agent for a period of time, e.g., 1 hour. Samples A and B are then each combined with (suggest amount) of genetically modified bacteriophage ϕA1122 comprising the recombinant bacteriophage marker gene: upstream gene ϕ13-LaqI$^q$-pTrc-rbs-gene ϕ13. Following an incubation of 10 minutes, aliquots from the exposed samples A and B are applied to LFI devices comprising first and second antibodies that specifically bind to the 15.8 kDa ϕA1122 head assembly protein in order to assay for the presence of the head assembly protein. The results from exposed samples A and B are compared. A decreased in the head assembly protein signal in exposed sample A indicates that the *Yersinia pestis* is susceptible to the agent.

SILAS Surface-Based Detection

Methods: Coated surfaces and HRP conjugated antibody are prepared using standard methods developed at Thermo Electron Corporation, 81 Wyman Street, Waltham, Mass. 02454-9046. Briefly, the surfaces are coated in a solution of HEPES buffer at pH 7.8 containing 4 ug/ml Rabbit anti-15.8 kDa ϕA1122 head assembly protein antibody for 48 hours. After coating, the wafers are washed and over-coated with a sugar:protein preservative, then divided into chips 7 mm square.

Conjugation proceeds according to a Thermo Electron modification of the method of Nakane. HRP is activated using sodium periodate to introduce aldehydes onto the carbohydrate portion of the protein. The activated HRP and the rabbit antibody are mixed and allowed to incubate. The conjugates are stabilized by adding sodium borohydride to reduce the Schiff's bases.

Testing is performed to determine the ability to detect the 15.8 kDa ϕA1122 head assembly protein provided. Initial formats include both simultaneous and sequential formats. The simultaneous format consists of mixing sample and conjugate (diluted 1:100 in conjugate diluent) and adding the sample to the surface of the coated OIA chip. Following incubation, the surface is washed and dried followed by addition of enzyme substrate (TMB). First and second incubations are kept equivalent at either 5 or 10 minutes. The sequential assay is similar to the simultaneous assay, except the sample and conjugate are not mixed but added to the chip independently. Incubation steps are separated by washing and blotting steps. The sequential assay is run using 10-minute incubations for all steps.

Results: The un-optimized methods described here are clearly able to detect the 15.8 kDa ϕA1122 head assembly protein in sample.

Example 3

Figure 3:
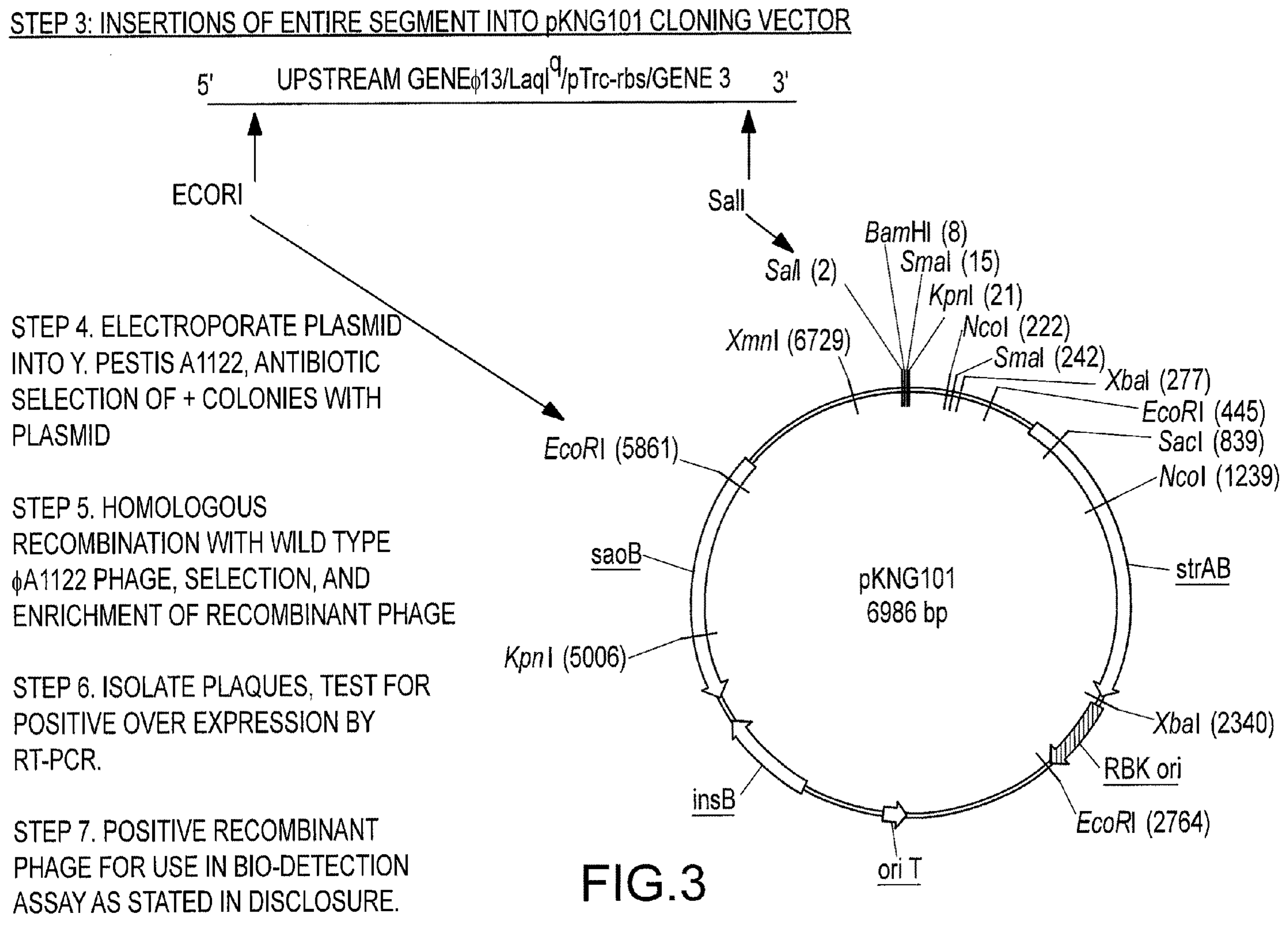
FIG. 3 shows cloning strategy for assembling a construct comprising upstream gene ϕ13, $LaqI^q$, pTrc-rbs, and gene ϕ13.

Construction of Genetically Modified Bacteriophage Comprising Recombinant Marker Gene for Upregulated Expression of Head Assembly Protein (FIGS. 1-3)

A recombinant bacteriophage marker gene for the over-expression of gene ϕ13 by genetically modified ϕA1122 is made for use in a detection assay for *Yersinia pestis.*

Step 1: PCR amplification of upstream gene 13, $LaqI^q$, pTrc-rbs, and gene ϕ13 is done using primers as described in FIG. 1.

Step 2: Insertions are done into cloning vector pBr322. 2a. PCR amplified DNA products are cleaned up and inserted into vector at indicated sites. 2b. pBR322 is ligated with insert with T4 DNA quick ligase. 2c. Vector with insert is cleaned up and checked by PCR.

Step 3. The entire segment is inserted into pKNG101 cloning vector.

Step 4. Plasmid is electroporated into *Yersinia pestis* ϕA1122, antibiotic selection of +colonies with plasmid is done.

Step 5. Homologous recombination with wild type ϕA1122 phage, selection, and enrichment of recombinant phage is done.

Step 6. Plaques are isolated and tested for positive over-expression by RT-PCR.

Step 7. Positive recombinant phage are used in bio-detection assay as described herein.

Example 4

Pretreatment/Sample Preparation for Direct Detection of Viral Major Capsid Protein (MCP)

Bacteriophage solutions with concentrations greater than $10^{10}$ pfu/ml were analyzed by combining ~100 μL of phage solution with 20 μL of β-mercaptoethanol (βME) and allowing the reaction to occur at room temperature for ten minutes prior to MALDI sample preparation. Reactions were allowed to progress 10, 30, 60, 120, and 180 minutes with no discernable difference in performance after ten minutes suggesting that the reaction occurs relatively rapidly as previously postulated. Casini et al.; *In vitro papillomavirus capsid assembly analyzed by light scattering*, (2004) Virology 325, pp 320-327. Volumes of βME added were varied from 10 μL-80 μL. While the whole range of volumes added is in excess the amount of 20 μL was chosen to optimize crystal formation in the MALDI sample preparation process. MALDI-TOF samples were prepared by first spotting 1 μL of ~10 mg/ml of ferulic acid in a 17:33:50 mixture of 88% formic acid, acetonitrile and de-ionized water solution, 1 μL of treated bacteriophage solution, and 1 μL of additional matrix solution in a sandwich fashion in triplicate on a stainless steel target. Drying was carried out between each addition in a vacuum dessicator.

Mass spectrometric measurements were carried out with a 337 nm $N_2$ laser in positive ion linear mode using a PerSeptive Biosystems Voyager-DE STR+MALDI-TOF-MS (Applied Biosystems, Inc. Framingham Mass., USA). Spectra were collected with 25 kV accelerating voltage, 75% grid voltage, and 100 ns acceleration delay. Spectra were collected for the triplicate spots with 250 shots per spectrum. Data was exported from Data Explorer (Applied Biosystems) into Sigmaplot v11.0 for plotting and spectral interpretation.

Figure 10A:
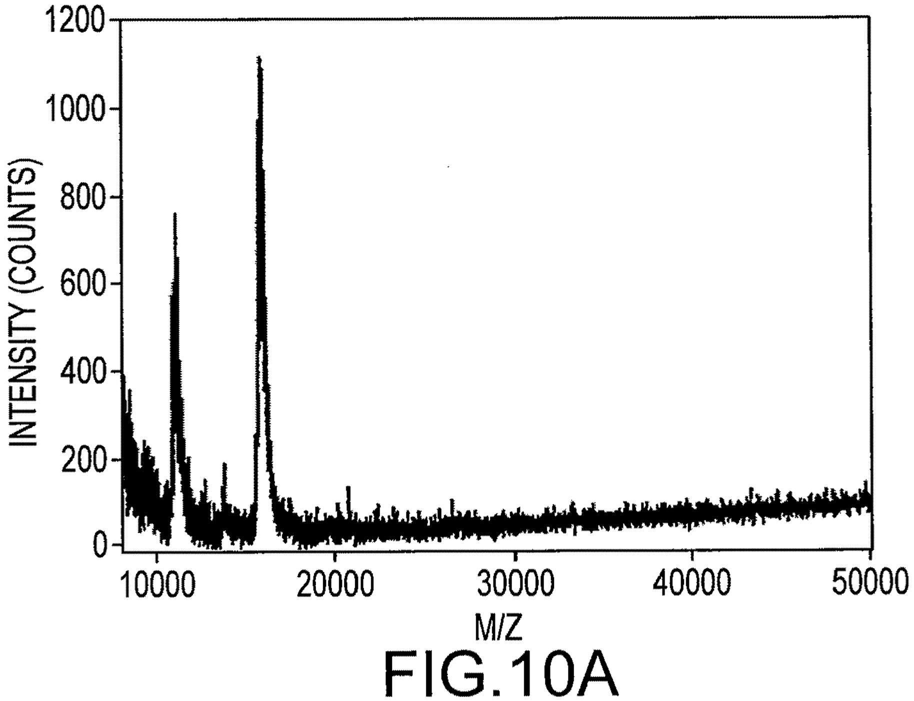
FIG. 10. MALDI spectra for ϕ-A1122 without (A) and with (B) pretreatment with β-mercapto ethanol.
Figure 10B:
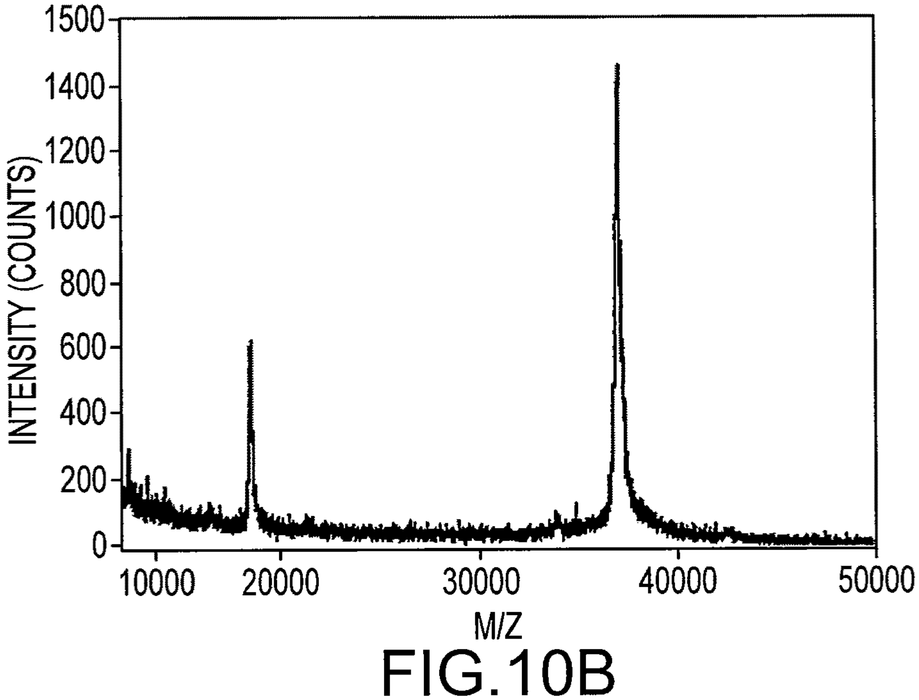

Results: FIG. 10 shows results from MALDI-TOF of the two samples. Visible in the sample prepared with βME is a peak at 37.5 k m/Z representing the capsid protein for this phage.

All citations are expressly incorporated herein in their entirety by reference.

We claim:

1. A method for determining the presence or absence of bacteria of a target bacterial type in a sample, comprising (i) contacting the sample with genetically modified bacteriophage that are selective for the target bacterial type under conditions that allow said genetically modified bacteriophage to infect said bacteria of the target bacterial type that may be present in said sample, thereby producing a bacteriophage exposed sample, wherein said genetically modified bacteriophage comprise a recombinant bacteriophage marker gene comprising a nucleic acid sequence encoding a bacteriophage marker operably linked to an expression control region that affects expression of said bacteriophage marker gene during the late eclipse or early latent period following infection of said bacteria of the target bacterial type by said genetically modified bacteriophage and results in overexpression of the bacteriophage marker gene;

(ii) incubating said bacteriophage exposed sample for a period of time sufficient to allow said genetically modified bacteriophage to infect said bacteria of the target bacterial type that may be present in said sample; and (iii) assaying said bacteriophage exposed sample for the bacteriophage marker encoded by said bacteriophage marker gene to detect the protein expressed from the bacteriophage marker gene, wherein said assaying step does not detect the presence of said bacteriophage marker in the bacteriophage exposed sample in the absence of bacterial infection, and wherein the presence of said bacteriophage marker indicates the presence of said bacteria of the target bacterial type in said sample, wherein said nucleic acid sequence encoding a bacteriophage marker encodes an endogenous head assembly protein, and wherein said expression control region affects overexpression of said bacteriophage marker gene encoding said endogenous head assembly protein, wherein said bacteriophage marker encoded by said bacteriophage marker gene is not accessible for detection on intact progeny phage, and wherein said target bacterial type is *Yersinia pestis*, and wherein said endogenous head assembly protein is the 15.8 kDa ϕA1122 head assembly protein.

2. The method according to claim 1, further comprising the use of a negative control, wherein steps (i)-(iii) are repeated with a control sample known to lack bacteria of the target bacterial type to confirm that said assaying step does not detect the presence of said bacteriophage marker in the bacteriophage exposed sample in the absence of bacterial infection.

3. The method according to claim 1, wherein said assaying step involves lysis of the bacteria.

4. The method according to claim 1, wherein said bacteria of the target bacterial type are present in said sample at a concentration of less than about 1000 cells/ml.

5. The method according to claim 1, wherein said incubation step comprises a period of time less than the time required to initiate a second cycle of infection by progeny of said genetically modified bacteriophage.

6. The method according to claim 1, wherein said incubation step comprises a period of time less than the replication time of said genetically modified bacteriophage.

7. The method according to claim 1, wherein said incubation step comprises a period of time less than about 45 minutes.

8. The method according to claim 1, wherein the period of time from said contacting step to the result of said assaying step comprises a period of time less than about 45 minutes.

9. The method according to claim 1, wherein said assaying step involves the use of at least one antibody to detect said bacteriophage marker.

10. The method according to claim 9, wherein said antibody is a monoclonal antibody.

11. The method according to claim 9, wherein said antibody is present on a lateral flow immunochromatography (LFI) apparatus or a SILAS surface.

12. The method according to claim 1, wherein said target bacterial type is *Yersinia pestis*, said genetically modified bacteriophage is a genetically modified ϕA1122, said nucleic acid sequence encoding a bacteriophage marker encodes a ϕA1122 endogenous head assembly protein, said expression control region affects overexpression of said bacteriophage marker gene encoding said endogenous head assembly protein following infection of *Yersinia pestis*.

13. The method according to claim 12, wherein said recombinant bacteriophage marker gene comprises upstream gene ϕ13-LaqI$^q$-pTrc-rbs-gene ϕ13.

* * * * *